US008318481B2

(12) United States Patent
Chew et al.

(10) Patent No.: US 8,318,481 B2
(45) Date of Patent: Nov. 27, 2012

(54) HIGH COPY NUMBER SELF-REPLICATING PLASMIDS IN PSEUDOMONAS

(75) Inventors: Lawrence C. Chew, San Diego, CA (US); Stacey L. Lee, San Diego, CA (US)

(73) Assignee: Pfenex Inc., San Diego, CA (US)

( * ) Notice: Subject to any disclaimer, the term of this patent is extended or adjusted under 35 U.S.C. 154(b) by 837 days.

(21) Appl. No.: 12/328,971

(22) Filed: Dec. 5, 2008

(65) Prior Publication Data
US 2009/0162898 A1 Jun. 25, 2009

Related U.S. Application Data

(60) Provisional application No. 61/012,236, filed on Dec. 7, 2007.

(51) Int. Cl.
*C12N 15/63* (2006.01)
*C12N 1/21* (2006.01)
*C07K 14/00* (2006.01)

(52) U.S. Cl. ............... 435/320.1; 530/350; 435/252.1

(58) Field of Classification Search ................ None
See application file for complete search history.

(56) References Cited

U.S. PATENT DOCUMENTS

| | | | |
|---|---|---|---|
| 4,511,503 | A | 4/1985 | Olson et al. |
| 4,551,433 | A | 11/1985 | DeBoer |
| 4,595,658 | A | 6/1986 | Zinder et al. |
| 4,637,980 | A | 1/1987 | Auerbach et al. |
| 4,695,462 | A | 9/1987 | Barnes et al. |
| 5,169,760 | A | 12/1992 | Wilcox |
| 5,169,772 | A | 12/1992 | Zimmerman et al. |
| 5,605,793 | A | 2/1997 | Stemmer |
| 5,811,238 | A | 9/1998 | Stemmer et al. |
| 5,830,721 | A | 11/1998 | Stemmer et al. |
| 5,837,458 | A | 11/1998 | Minshull et al. |
| 6,864,087 | B2 | 3/2005 | Szybalski et al. |
| 2004/0235121 | A1 | 11/2004 | Smider |
| 2005/0130307 | A1 | 6/2005 | Cheng et al. |
| 2006/0008877 | A1 | 1/2006 | Retallack et al. |
| 2006/0014257 | A1 | 1/2006 | Katashkina et al. |

FOREIGN PATENT DOCUMENTS

| | | |
|---|---|---|
| EP | 0155189 | 9/1985 |
| EP | 0288451 | 10/1988 |
| WO | WO-03-068926 | 8/2003 |
| WO | WO-03-068948 | 8/2003 |
| WO | WO-03-089455 | 10/2003 |
| WO | WO-2004-005221 | 1/2004 |
| WO | WO 2005/028623 A2 | 3/2005 |
| WO | WO-2009-076196 | 6/2009 |

OTHER PUBLICATIONS

Arai, H., et al., "Construction of Novel Expression Vectors Effective in *Pseudomonas* Cells,"*Agric. Biol. Chem.*, 1991, 55(9), 2431-2432.
Bagdasarian, M., et al., "Specific-Purpose Plasmid Cloning Vectores, II. Broad Host Range, High Copy Number, RSF1010-Derived Vectors, and a Host-Vector System for Gene Cloning in Pseudomonas," *Gene.*, 1981, Abstract.
Gao, et al., "Copy Number Determination and Restriction Map of Plasmid pNK866," *Acta Microbiologica Sinica*, 1994, 34(1): Abstract.
Garcia De Viedma, et al., "Transcription of repA, the Gene of the Initiation Protein of the Pseudomonas Plasmid pPS10, is Autoregulated by Interactions of the RepA Protein at a Symmetrical Operator," *J. Mol. Biol.*, 1995, 247, 211-223.
Giraldo, R., et al., "Protein Domains and Conformational Changes in the Activation of RepA, a DNA Replication Initiator," *The EMBO Journal*, 1998, 17(15), 4511-4526.
Haugan, K, et al., "The Host Range of RK2 Minimal Replicon Copy-Up Mutants is Limited by Species-Specific Differences in the Maximum Tolerable Copy Number," *Plasmid*, 1995, 33, 27-39.
Heeb, S., et al., "Small, Stable Shuttle Vectors Based on the Minimal pVS1 Replicon for Use in Gram-Negative, Plant-Associated Bacteria," *MPMI*, 2000, 13(2), 232-237.
Itoh, N., et al., "Novel Plasmid Vectors for Gene Cloning in *Pseudomonas*," 1991, *J. Biochem*, 110, 614-621.
Itoh, Y., et al., "Low- and Intermediate-Copy-Number Cloning Vectors Based on the *Pseudomonas* Plasmid pVS1," 1988, *Antónie van Leeuwenhoek*, 1988, 54, 567-573.
Diaz-Lopez, T., et al., "Structural Changes in RepA, a Plasmid Replication Initiator, Upon Binding to Origin DNA," *J. Biol. Chem.*, 2003, 278(20), 18606-18616.
Maestro, B., et al., Modulation of pPS10 Host Range by Plasmid-Encoded RepA Initiator Protein, *Journal of Bacteriology*, 2003, 185(4), 1367-1375.
Nieto, C., et al., Cloning Vectors, Derived From a Naturally Occurring Plasmid of *Pseudomonas savastanoi*, Specifically Tailored for Genetic Manipulations in *Pseudomonas*, *Gene*, 1990, 87, 145-149, Elsevier Science Publishers B.V. (Biomedical Division).
Nieto, C., et al., "Genetic and Functional Analysis of the Basic Replicon of pPS10, a Plasmid Specific for *Pseudomonas* Isolated from *Pseudomonas, syringae patovar savastanoi,*" *J. Mol. Biol*, 1992, 223, 415-426.
EMBL Database Accession No. X58896, Submitted Mar. 17, 1992.
Uniprot Database Accession No. Q52546, 2009.

(Continued)

*Primary Examiner* — Michele K Joike
(74) *Attorney, Agent, or Firm* — Wilson, Sonsini, Goodrich & Rosati

(57) ABSTRACT

Provided herein are improved copy number plasmids, particularly those plasmids capable of replication in a bacterial cell. The improved copy number plasmid contain a deletion, insertion, or substitution in the replication control region, particularly a *Pseudomonas*-specific replication control region, that results in an increase in plasmid copy number in comparison to a control plasmid. Also provided are host cells containing the improved copy number plasmids, as well as methods of using the improved copy number plasmids for the recombinant production of a protein of interest. Further provided are methods for generating plasmids with improved copy number. The methods disclosed herein involve the reiterative selection of improved copy number plasmids by the growth and selection of plasmids capable of growth under increasing selective pressure, wherein the selective pressure is applied utilizing a selection agent to which the control plasmid confers resistance.

23 Claims, 6 Drawing Sheets

OTHER PUBLICATIONS

Giraldo et al. "Twenty years of the pPS10 replicon: insights on the molecular mechanism for the activation of DNA replication in iteron-containing bacterial plasmids." *Plasmid*, 2004, 52:69-83.

Xia et al. "In Vivo and In Vitro Studies of a Copy Number Mutation of the RepA Replication Protein of Plasmid pSC101." *Journal of Bacteriology*, Jul. 1993, 175(13):4165-4175.

PCT/US2008/085664 IPRP and Written Opinion dated Jun. 8, 2010.

U.S. Appl. 60/887,476, filed Jan. 31, 2007, Schneider.

U.S. Appl. 60/887,486, filed Jan. 31, 2007, Schneider.

Agarraberes and Dice, "Protein translocation across membranes," Biochim Biophys Acta 1513:1-24 (2001).

Ames et al., "Simple, Rapid, and Quantitative Release of Periplasmic Proteins by Chloroform," J. Bacteriol, 160:1181-1183 (1984).

Ariga et al., "Release of thermophilic α-amylase from transformed *Escherichia coli* by addition of glycine" J. Ferm. Bioeng. 68:243-246 (1989).

Asami et al., "Synchronized Disruption of *Escherichia coli* Cells by T4 Phage Infection," J. Ferment. and Bioeng., 83:511-516 (1997).

Bagdasarian and Timmis, "Host: Vector Systems for Gene Cloning in Pseudomonas," *Curr. Topics Microbiol. Immunol.*, 1982, 96:47-67.

Baldwin, "Comparison of transferrin sequences from different species," Comp. Biochem Physiol., 106(1):203-218 (1993).

Benoist and Chambon, "In vivo sequence requirements of the SV40 early promoter region," Nature 290:304-310 (1981).

Blattner et al., "The complete genome sequence of *Escherichia coli* K-12," Science 277(5331):1453-74(1997).

Broxmeyer et al., "Menocyte-Macrophage-Derived Acidic Isoferritins: Normal Feedback Regulators of Granulocyte-Macrophage Progenitor Cells in Vitro," Blood 60:595 (1982).

Buchanan and Gibbons (eds). *Bergey's Manual of Determinative Bacteriology*, 8th ed., 1974, pp. 217-289, The Williams & Wilkins Co, Baltimore, MD.

Cabello et al., "Replication control in a composite plasmid constructed by in vitro linkage of two distinct replicons, " Nature, 259:285-290 (1976).

Carter et al., "High level *Escherichia coli* expression and production of a bivalent humanized antibody fragment," Biotechnology, 10(2):163-167 (1992).

Coombs et al., "Site-Directed Mutagenesis and Protein Engineering," Proteins, 259-311, 1 plate, Ed.: Angeletti, Ruth Hogue. Academic: San Diego, Calif. (1998).

Dabora and Cooney, "Intracellular Lytic Enzyme Systems and Their Use for Disruption of *Escherichia coli*," Advances in Biochemical Engineering/Biotechnology, vol. 43, pp. 11-30, A. Fiechter, ed. (Springer-Verlag, Berlin)(1990).

Davis and Mingioli, "Mutants of *Escherichia Coli* Requiring Methionine or Vitamin $B_{12}$," *J. Bact.*, 1950, 60:17-28.

Del Solar et al., "Replication and Control of Circular Bacterial Plasmids," Microbiology and Molecular Biology Reviews, vol. 62, No. 2, pp. 434-464 (1998).

Drake et al., "Rates of Spontaneous Mutation," Genetics, 148:1667-1686 (1998).

French et al., "Development of a simple method for the recovery of recombinant proteins from the *Escherichia coli* periplasm," Enzyme and Microb. Tech., 19:332-338 (1996).

Furlong and Sundstrom, "Immobilized cell bioreactors for producing immobilized protein bioadsorbers," Developments in Indus. Microbio. 30:141-8 (1989).

Garcia De Viedma et al., "A leucine zipper motif determines difference functions in a DNA replication protein, " EMBO Journal, vol. 15, No. 4, pp. 925-934 (1996).

Ginzinger, D.J., "Gene quantification using real-time quantitative PCR: an emerging technology hits the mainstream." Experimental Hematology, 30(6):503-512 (2002).

Giraldo et al., "A conformational switch between transcriptional repression and replication initiation in the RepA dimarization domain," Nature Structural Biology, vol. 10, No. 7, pp. 565-571 (2003).

Giraldo et al., "Similarities between the DNA replication initiators of Gram-negative bacteria plasmids (RepA) and eukaryotes (Orc4p)/archaea (Cdc6p)," PNAS, vol. 98, No. 9, pp. 4938-4943 (2001).

Gruss et al., "Simian virus 40 tandem repeated sequences as an element of the early promoter," Proc. Nat. Acad. Sci. 78(2):943-947 (1981).

Hancock and Poxton, Isolation and Purification of Cell Walls, Bacterial Cell Surface Techniques (John Wiley and Sons Ltd., 1988) Chapter 3. p. 55.

Hochuli "Purification of Recombinant Proteins with Metal Chelate Absorbent." *Genetic Engineering, Priniciple and Methods*, 12:87-98, 1990, Setlow, ed., Plenum Press, NY.

Hsiung et al., "Use of Bacteriocin Release Protein in *E. Coli* for Excretion of Human Growth Hormone into the Culture Medium," Bio/Technology 7:267-71 (1989).

Jeong and Lee, "Excretion of Human β-Endorphin into Culture Medium by Using Outer Membrane Protein F as a Fusion Partner in Recombinant *Escherichia coli*," Appl Environ. Microbio. 68:4979-4985 (2002).

Joseph-Liazun et al., "Human recombinant interleukin-1β isolated from *Escherichia coli* by simple osmotic shock," Gene, 86:291-295 (1990).

Khoury and Gruss, "Enhancer Elements" Cell 33:313-314 (1983).

Kodama et al., "The Initial Phosphate Burst in ATP Hydrolysis by Myosin and Subfragment-1 as Studied by a Modified Malachite Green Method for Determination of Inorganic Phosphate," J. Biochem, 99 :1465-1472 (1986).

Lawn et al., "The sequence of human serum albumin cDNA and its expression in *E. coli*," Nucleic Acids Research, 9:6103-6114 (1981).

Leung et al., "A Method for Random Mutagenesis of a Defined DNA Segment Using a Modified Polymerase Chain Reaction," Technique, 1:11-15 (1989).

Lloubes et al., "Colicin A lysis protein promotes extracellular release of active human growth hormone accumulated in *Escherichia coli* cytoplasm," Biochimie 75:451-8 (1993).

Lombillo et al., "Antibodies to the Kinesin Motor Doman and CENP-E Inhibit Microtubule Depolymerization-dependent Motion of Chromosomes in Vitro," J. Cell. Biol. 128 :107-115 (1995).

Lundell et al., "Cytoplasmic and periplasmic expression of a highly basic protein, human interleukin 4, n *Escherichia coli*," J. Indust. Microbio. 5:215-228 (1990).

Melnikov et al., "Random mutagenesis by recombinational capture of PCR products in *Bacillus subtilis* and *Acinetobacter calcoaceticus*," Nucleic Acids Research, 27(4):1056-1062 (1999).

Messing et al., "Plant Gene Structure" in Genetic Engineering of Plants (Kosuge et al., eds.), pp. 211-227 (1983).

Miksch et al., "The kil gene of the COLE1 plasmid of *Escherichia coli* controlled by a growth-phase-dependent promoter mediates the secretion of a heterologous periplasmic protein during the stationary phase," Arch. Microbiol. 167:143-150 (1997).

Mukhija et al., "High-level production and one-step purification of biologically active human growth hormone in *Escherichia coli*," Gene, 1995, 165(2):303-306.

Muller et al., "Protein Traffic in Bacteria: Multiple Routes from the Ribosome to and Across the Membrane," Prog Nucleic Acid Res Mol. Biol. 66:107-157 (2001).

Naglak and Wang, "Recovery of a foreign protein from the periplasm of *Escherichia coli* by chemical permeabilization," Enzyme Microb. Technol., 12:603-611 (1990).

Neu and Heppel, "The Release of Ribonuclease into the Medium when *Escherichia coli* Cells are Converted to Spheroplasts," J. Biol. Chem., 239:3893-3900 (1964).

Neu and Heppel, "The Release of Enzymes from *Escherichia coli* by Osmotic Shock and during the Formation of Spheroplasts," J. Biol. Chem., 240:3685-3692 (1965).

Nossal and Heppel, "The Release of Enzymes by Osmotic Shock from *Escherichia coli* in Exponential Phase," J. Biol. Chem., 241:3055-3062 (1966).

Patra et al., "Optimization of Inclusion Body Solubilization and Renaturation of Recombinant Human Growth Hormone from *Escherichia coli*," Protein Expr Purif. 18(2) : 182-92 (2000).

Ralph et al., "Human B Cell-Inducing Factor(s) for Production of IgM, IgG and IgA: Independence from IL 2," J. Immunol. 132 :1858 (1984).

Retallack et al., "Trasnsport of heterologous proteins to the periplasmic space of Pseudomonas fluorescens using a variety of native signal sequences," Biotech Letters, 29(10):1483-1491 (2007).

Saiki et al., "Induction of Human Immunoglobulin Secretion," J. Immunol. 127:1044 (1981).

Sanchez-Romero and De Lorenzo. "Genetic Engineering of Nonpathogenic Pseudomonas strains as Biocatalysts for Industrial and Environmental Processes." *Manual of Industrial Microbiology and Biotechnology*, 1999, pp. 460-474, Demain and Davies, Eds., ASM Press, Washington, D.C.

Schmittgen, T., "Real Time Quantitative PCR," Methods, 25(4):383-481 (2001).

Schweizer. H. "Vectors to express foreign genes and techniques to monitor gene expression for Pseudomonads." *Current Opinion in Biotechnology*, 2001, 12(5):439-445.

Scorer et al., "Rapid selection using G418 of high copy number transformants of *Pichia pastoris* for high-level foreign gene expression," Biotechnology 12(2):181-4 (1994).

Sheldon AT Jr., "Antibiotic resistance: a survival strategy." Clin Lab Sci 18(3): 170-180 (2005).

Shokri et al., "Growth rate-dependent changes in *Escherichia coli* membrane structure and protein leakage," App Microbial Biotechnol 58:386-392 (2002).

Simmons et al., "Expression of full-length immunoglobulins in *Escherichia coli*: rapid and efficient production of aglycosylated antibodies," J. Immun. Meth. 263:133-147 (2002).

Slater and Williams. The Expression of Foreign DNA in Bacteria, *Molecular Biology and Biotechnology*, 2000, pp. 125-154, Walker and Rapley, eds., The Royal Society of Chemistry, Cambridge, UK.

Spee et al., "Efficient random mutagenesis method with adjustable mutation frequency by use of PCR and dITP," Nucleic Acids Res., 21:777-778 (1993).

Stabel et al., "Periplasmic location of *Brucella abortus* Cu/Zn superoxide dismutase," Veterinary Microbiol., 38:307-314 (1994).

Stewart et al., "Direction of microtubule movement is an intrinsic property of the motor domains of kinesin heavy chain and *Drosophila ncd* protein," Proc. Nat'l. Acad. Sci 90:5209-5213 (1993).

Stratagene, "XL1-Red: A Highly Efficient Random Mutagenesis Strain," La Jolla, CA; Greener and Callahan, Strategies, 7:32-34 (1994).

Taguchi et al., "Comparison of secretory expression in *Escherichia coli* and Streptomyces of Streptomyces subtilisin inhibitor (SSI) gene," Biochimica Biophysica Acta 1049:278-85 (1990).

Tanji et al. "Controlled Expression of Lysis Genes Encoded in T4 Phage for the Gentle Disruption of *Escherichia coli* Cells," J. Ferment. and Bioeng., 85:74-78 (1998).

Uhlin et al. "R plasmid gene dosage effects in *Escherichia coli* K-12: Copy Mutants of the R plasmid R1drd-19," Plasmid, Nov;1(1):1-7 (1977).

Vale et al., "Identification of a Novel Force-Generating Protein, Kinesin, Involved in Mucrotubule-Based Motility," Cell 42:39-50 (1985).

Wan and Baneyx, "TolAIII Co-overexpression Facilitates the Recovery of Periplasmic Recombinant Proteins into the Growth Medium of *Escherichia coli*," Protein Expression Purif, 14:13-22 (1998).

Witholt et al., "How Does Lysozyme Penetrate Through the Bacterial Outer membrane?" Biochim Biophys Acta 443:534-544 (1976).

Yang et al., "Human transferrin: cDNA characterization and chromosomal localization," Proc. Natl. Acad. Sci. 81:2752-2756 (1984).

Zhou et al., "Random mutagenesis of gene-sized DNA molecules by use of PCR with Taq DNA polymerase," Nucleic Acids Research, 19:6052 (1991).

Zinder and Arndt, "Production of Protoplasts of *Escherichia coli* by Lysozyme Treatment," Proc. Natl. Acad. Sci, 42:586-590 (1956).

PCT/US2008/085664 Search Report dated Mar. 23, 2009.

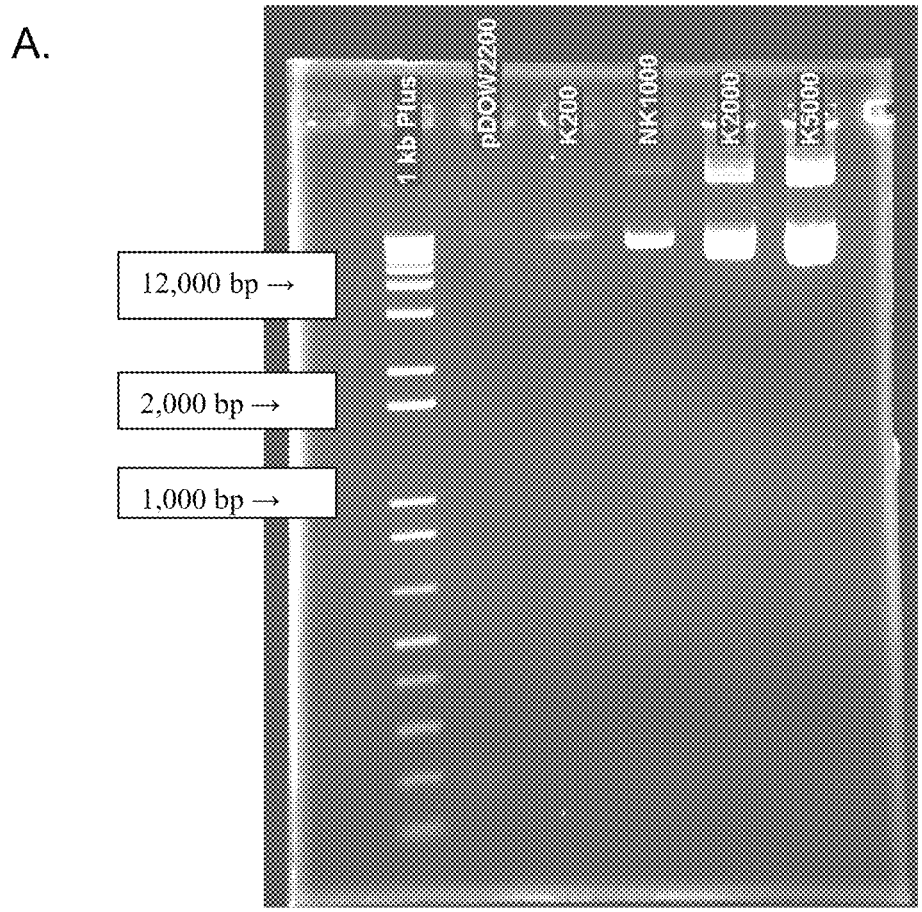
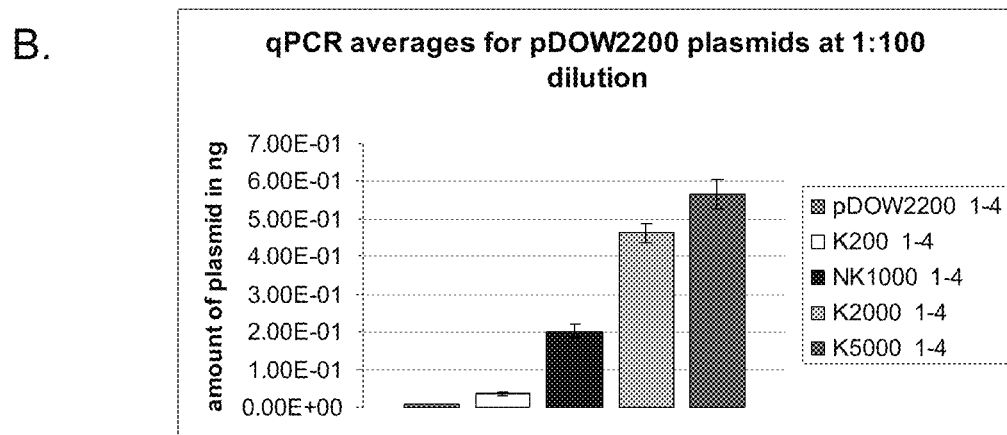
FIG. 3

```
          1                                                         50
2200repA  atggtcgaga acaaagtcac gcagtccaat aaactcatcg aatcgtcaca
2426repA  atggtcgaga acaaagtcac gcagtccaat aaactcatcg aatcgtcaca
2427repA  atggtcgaga acaaagtcac gcagtccaat aaactcatcg aatcgtcaca 51                                                        100
2200repA  tacgttgaca ctcaatgaga aacgcctagt gctatgcgct gcgtctttga
2426repA  tacgttgaca ctcaatgaga aacgcctagt gctatgcgct gcgtctttga
2427repA  tacgttgaca ctcaatgaga aacgcctagt gctatgcgct gcgtctttga 101                                                       150
2200repA  tcgattcacg taagccactc cctaaagatg gttacttgac catccgagct
2426repA  tcgattcacg taagccactc cctaaagatg gttacttgac catccgagct
2427repA  tcgattcacg taagccactc cctaaagatg gttacttgac catccgagct 151                                                       200
2200repA  gacaccttcg ctgaggtgtt tggaattgat gtcaaacacg cctatgcggc
2426repA  gacaccttcg ctgaggtgtt tggaattgat gtcaaacacg cctatgcggc
2427repA  gacaccttcg ctgaggtgtt tggaattgat gtcaaacacg cctatgcggc 201                                                       250
2200repA  attagatgac gctgccacaa agttgtttaa ccgacatatt cgcaggtacg
2426repA  attagatgac gctgccacaa agttgtttaa ccgacatatt cgcaggtacg
2427repA  attagatgac gctgccacaa agttgtttaa ccgacatatt cgcaggtacg 251                                                       300
2200repA  tcaaaggcaa agtcgttgaa cgcatgcgct gggttttttca cgtcaagtac
2426repA  tcaaaggcaa agtcgttgaa ggcatgcgct gggttttttca cgtcaagtac
2427repA  tcaaaggcaa agtcgttgaa cgcatgctct gggttttttca cgtcaagtac 301                                                       350
2200repA  agggaaggcc aaggctgcgt cgagctagga ttttctccta cgataatccc
2426repA  agggaaggcc aaggctgcgt cgagctagga ttttctccta cgataatccc
2427repA  agggaaggcc aaggctgcgt cgagctagga ttttctccta cgataatccc 351                                                       400
2200repA  gcatctaacc atgctgcaca aagagttcac cagctatcag ctcaagcaaa
2426repA  gcatctaacc atgctgcaca aagagttcac cagctatcag ctcaagcaaa
2427repA  gcatctaacc atgctgcaca aagagttcac cagctatcag ctcaagcaaa 401                                                       450
2200repA  tcggtagcct gtccagcttc tacgctgtcc gcctttacga gcttatgagc
2426repA  tcggtagcct gtccagcttc tacgctgtcc gcctttacga gcttatgagc
2427repA  tcggtagcct gtccagcttc tacgctgtcc gcctttacga gcttatgagc 451                                                       500
2200repA  caatttatca agctcaaaca gcgggaatgc acactcgccc aactgcggga
2426repA  caatttatca agctcaaaca gcgggaatgc acactcgccc aactgcggga
2427repA  caatttatca agctcaaaca gcgggaatgc acactcgccc aactgcggga 501                                                       550
2200repA  aatgttcgac cttggtgaca agtaccaaga cgttaaggac atgcgtaagc
2426repA  aatgttcgac cttggtgaca agtaccaaga cgttaaggac atgcgtaagc
2427repA  aatgttcgac cttggtgaca agtaccaaga cgttaaggac atgcgtaagc 551                                                       600
2200repA  gtgtgctata tcccgcttta gaggaagtga acaagaacac cgatttgaca
2426repA  gtgtgctata tcccgcttta gaggaagtga acaagaacac cgatttgaca
2427repA  gtgtgctata tcccgcttta gaggaagtga acaagaacac cgatttgaca 601                                                       650
2200repA  gtggcagtgg agcctcgccg acagggccga cgaatcattg ggttctcatt
2426repA  gtggcagtgg agcctcgccg acagggccga cgaatcattg ggttctcatt
2427repA  gtggcagtgg agcctcgccg acagggccga cgaatcattg ggttctcatt 651                                         690
2200repA  cacgatcgct aaaaacgatc aactggcact gagtctcgag
2426repA  cacgatcgct aaaaacgatc aactggcact gagtctcgag
2427repA  cacgatcgct aaaaacgatc aactggcact gagtctcgag
```

FIG. 4

```
                       1                                                    50
2200repApro  mvenkvtqsn  kliesshtlt  lnekrlvlca  aslidsrkpl  pkdgyltira
2426repApro  mvenkvtqsn  kliesshtlt  lnekrlvlca  aslidsrkpl  pkdgyltira
2427repApro  mvenkvtqsn  kliesshtlt  lnekrlvlca  aslidsrkpl  pkdgyltira 51                                                   100
2200repApro  dtfaevfgid  vkhayaaldd  aatklfnrdi  rryvkgkvve  rmrwvfhvky
2426repApro  dtfaevfgid  vkhayaaldd  aatklfnrdi  rryvkgkvve  gmrwvfhvky
2427repApro  dtfaevfgid  vkhayaaldd  aatklfnrdi  rryvkgkvve  rmlwvfhvky 101                                                   150
2200repApro  regqgcvelg  fsptiiphlt  mlhkeftsyq  lkqigslssf  yavrlyelms
2426repApro  regqgcvelg  fsptiiphlt  mlhkeftsyq  lkqigslssf  yavrlyelms
2427repApro  regqgcvelg  fsptiiphlt  mlhkeftsyq  lkqigslssf  yavrlyelms 151                                                   200
2200repApro  qfiklkqrec  tlaqlremfd  lgdkyqdvkd  mrkrvlypal  eevnkntdlt
2426repApro  qfiklkqrec  tlaqlremfd  lgdkyqdvkd  mrkrvlypal  eevnkntdlt
2427repApro  qfiklkqrec  tlaqlremfd  lgdkyqdvkd  mrkrvlypal  eevnkntdlt 201                       230
2200repApro  vaveprrqgr  riigfsftia  kndqlalsle
2426repApro  vaveprrqgr  riigfsftia  kndqlalsle
2427repApro  vaveprrqgr  riigfsftia  kndqlalsle
```

FIG. 5

HIGH COPY NUMBER SELF-REPLICATING PLASMIDS IN PSEUDOMONAS

CROSS-REFERENCE TO RELATED APPLICATIONS

This application claims the benefit of U.S. Provisional Application No. 61/012,236, filed Dec. 7, 2007, which is hereby incorporated in its entirety by reference herein.

FIELD OF THE INVENTION

This invention is in the field of molecular biology and cloning vectors, particularly plasmid vectors with improved copy number.

REFERENCE TO SEQUENCE LISTING SUBMITTED ELECTRONICALLY

The official copy of the sequence listing is submitted electronically via EFS-Web as an ASCII formatted sequence listing with a file named "363155_SequenceListing.txt", created on Dec. 2, 2008, and having a size of 21 kilobytes and is filed concurrently with the specification. The sequence listing contained in this ASCII formatted document is part of the specification and is herein incorporated by reference in its entirety.

BACKGROUND OF THE INVENTION

More than 150 recombinantly produced proteins and polypeptides have been approved by the U.S. Food and Drug Administration (FDA) for use as biotechnology drugs and vaccines, with another 370 in clinical trials. Proteins tested to date come from both prokaryotic and eukaryotic sources and are quite varied in both structure and function. Optimizing expression for a wide variety of proteins involves testing and usage of a multitude of factors which can affect transcription, translation, solubility and stability of the protein of interest. Factors which can affect protein expression are environmental (eg. temperature or nutrients), host cell specific (eg. protease deficiency or chaperone overexpression) or plasmid specific (eg. type of promoter or plasmid copy number).

One means to increase gene expression involves increasing the number of copies of the plasmid from which the gene is transcribed, either by increasing the number of copies of the cloned gene within each expression plasmid or by increasing the copy number of the plasmid on which the gene to be expressed resides. It is known that plasmids must control their replication so that the copy number (N) of a given plasmid within a population of cells is usually maintained within a narrow Gaussian distribution within a given host and under defined growth conditions. This control is required, since plasmids must co-exist stably within their hosts and minimize metabolic load upon the cell. Specifically, over-accumulation of plasmid copies within a cell can slow cell growth and eventually cause cell death.

SUMMARY OF THE INVENTION

Provided herein are improved copy number plasmids, particularly those plasmids capable of replication in a bacterial cell. The improved copy number plasmid comprises a deletion, insertion, or substitution in the replication control region that results in an increase in plasmid copy number in comparison to a control plasmid. In some embodiments, the plasmid comprises a *Pseudomonas*-specific replication control region, and the mutation occurs in this region of the plasmid. In another embodiment, the replication control region encodes a RepA protein, and the mutation occurs in the repA gene. Also provided are host cells comprising the improved copy number plasmids, as well as methods of using the improved copy number plasmids for the recombinant production of a protein of interest.

Also provided herein are methods for generating plasmids with improved copy number. The methods of the present invention involve the reiterative selection of improved copy number plasmids by the growth and selection of plasmids capable of growth under increasing selective pressure, wherein the selective pressure is applied utilizing a selection agent to which the control plasmid confers resistance, and wherein the amount of the selection agent is increased with each successive round of growth and selection.

BRIEF DESCRIPTION OF THE FIGURES

FIG. 3a shows an agarose gel image of plasmid maxiprep DNA prepared from O.D. normalized cell cultures. Each lane shows 1 μl of DNA from each plasmid prepared: Lane 1: 1 Kb Plus DNA Ladder, Lane 2: pDOW2200 (control), Lane 3: putative mutant plasmid K200, Lane 4: putative mutant plasmid NK1000, Lane 5: putative mutant plasmid K2000 Lane 6: putative mutant plasmid K5000. FIG. 3b shows the qPCR results using DNA shown in FIG. 3a. Error bars show variation of computed yields among the four repeats per sample.

FIG. 4 is a sequence alignment of the repA gene from the parent plasmid pDOW2200 (SEQ ID NO:1) and mutants NK1000 or pDOW2426 (SEQ ID NO:3) and K2000 or pDOW2427 (SEQ ID NO:5). NK1000 (pDOW2426) shows a C to G conversion at bp 271 and K2000 (pDOW2427) shows a G to T conversion at bp 278.

FIG. 5 is an amino acid alignment of the RepA gene from the parent plasmid pDOW2200 (SEQ ID NO:2) and mutants NK1000 or pDOW2426 (SEQ ID NO:4) and K2000 or pDOW2427 (SEQ ID NO:6). The C to G conversion in NK1000 (pDOW2426) results in an arginine to glycine change at amino acid 91. The G to T conversion in K2000 (pDOW2427) results in an arginine to leucine change at amino acid 93.

DETAILED DESCRIPTION

Overview

Figure 1:
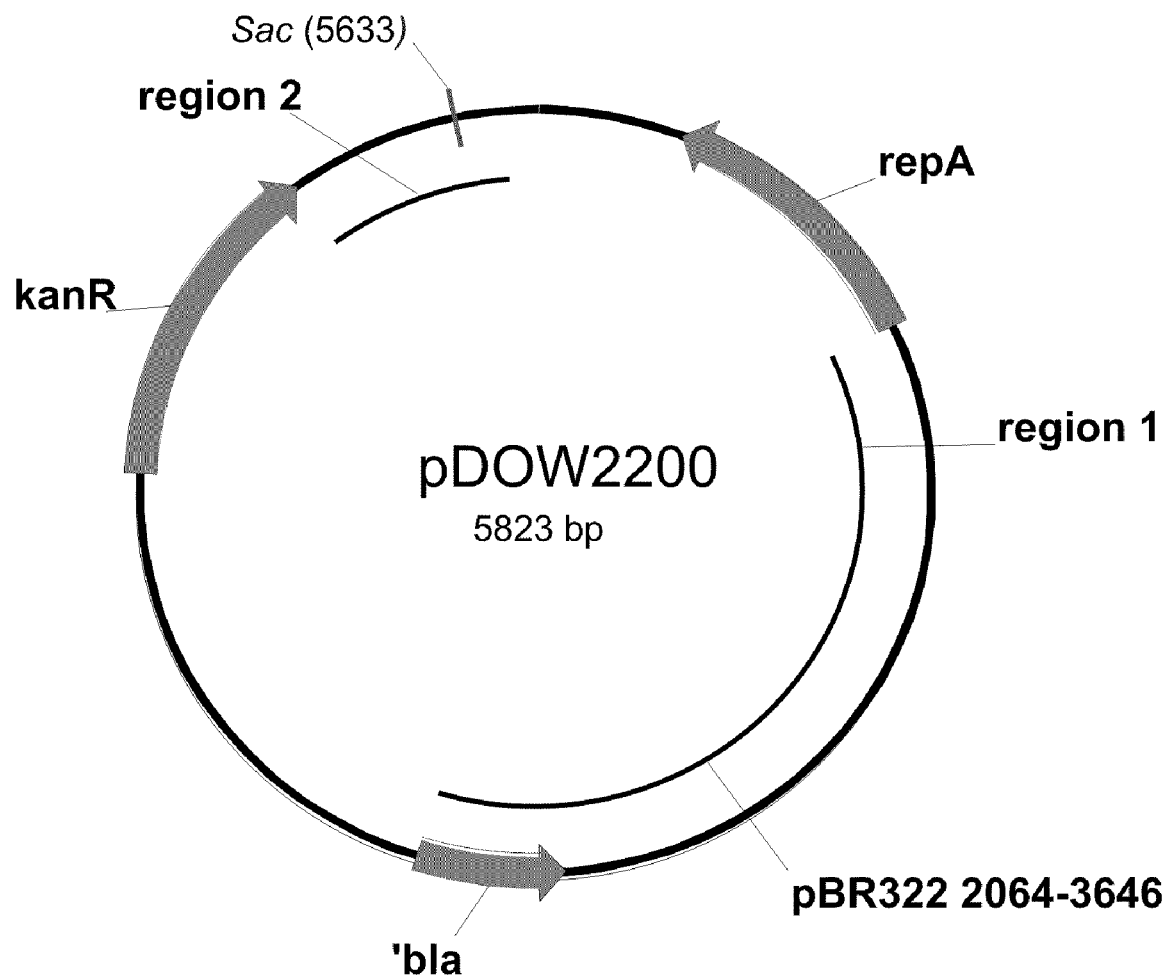
FIG. 1 depicts a plasmid map of pDOW2200.

Plasmids are commonly used as vectors for the cloning and expression of heterologous genes in bacteria. It is particularly desirable, for this purpose, to use plasmids that are present at an improved copy number, either in order to obtain the heterologous DNA in large quantities, or in order to increase the quantity and/or quality of heterologous protein expressed from the plasmid. For the purposes of the present invention, the terms "plasmid," "vector" and "cassette" refer to an extra-chromosomal element often carrying genes which are not part of the central metabolism of the cell, and usually in the form of circular, double-stranded DNA molecules. The term "plasmid copy number" refers to the average number of molecules of a plasmid contained within a cell.

Provided herein are improved copy number plasmids, particularly those plasmids capable of replication in a bacterial cell. An "improved copy number plasmid" as used herein refers to a plasmid that comprises a replication control region that results in an increase in plasmid copy number in comparison to a control plasmid. For the purposes of the present invention, a "control plasmid" refers to a plasmid comprising the replication control region set forth in SEQ ID NO:1, or a plasmid comprising a nucleotide sequence encoding the replication control region amino acid sequence set forth in SEQ ID NO:2. The term "replication control region" refers to a region of DNA containing a rep gene or a gene having homology to a rep gene that is responsible for controlling the replication, and affecting the plasmid copy number.

For the purposes herein, the plasmid copy numbers of mutant plasmids are compared relative to the non-mutagenized parent plasmid (e.g. "control plasmid"). However, the control plasmid can also be a mutagenized plasmid that is being subjected to additional mutagenesis methods described elsewhere herein with the intention of further improving the plasmid copy number. In one embodiment, the control plasmid is derived from the *Pseudomonas* plasmid pPS10 and the improved copy number plasmid results from a mutation (e.g., insertion, deletion, or substitution) in the replication control region of this plasmid.

In some embodiments, the plasmid comprises a *Pseudomonas*-specific replication control region, and the mutation occurs in this region of the plasmid. In another embodiment, the replication control region encodes a RepA protein, and the mutation occurs in this region. RepA protein is the DNA replication initiator of the *Pseudomonas* plasmid pPS10. Such mutations typically occur within the region defined as positions 200 to 400 as determined with reference to SEQ ID NO:1. In some embodiments, the mutation is within the region defined as positions 250 to 350, or positions 250 to 300, as determined with reference to SEQ ID NO:1. In another embodiment, the mutation is within the region encoding amino acid residues 60 to 130 as determined with reference to SEQ ID NO:2. In other embodiments, the mutation is within the region encoding amino acid residues 80 to 120, or amino acids 90 to 100, as determined with reference to SEQ ID NO:2.

The deletion, insertion, or substitution may involve one or more positions. The deletions can be of any length, e.g., 1 to 150 base pairs, but are typically less than 100 base pairs. Similarly, the insertions may be of any length, but are typically from 1 to 100 base pairs. Substitution can occur at one or more positions, e.g., 2, 3, 4, 5, 6, 7, 8, 9, 10, 11, 12, 15, 20, 30, 40, 50, or 100 positions. Additionally, multiple mutations and combinations of substitutions, insertions and/or deletions can also be present in replication control region described herein. In one embodiment, the plasmid comprises the replication control region sequence set forth in SEQ ID NO:3 or 5. In another embodiment, the plasmid comprises a replication control region nucleotide sequence encoding the amino acid sequence set forth in SEQ ID NO:4 or 6.

Compositions

Provided herein are improved copy number plasmids, wherein the replication control region of the plasmid has been altered with respect to a control plasmid. Generally, the plasmid will include origins of replication and selectable markers permitting transformation of the host cell and a promoter to direct transcription of the gene encoding the protein of interest.

In one embodiment, the plasmid comprises a polynucleotide sequence encoding a protein of interest operably linked to a promoter. Expressible coding sequences will be operatively attached to a transcription promoter capable of functioning in the chosen host cell, as well as all other required transcription and translation regulatory elements. The term "operably linked" refers to any configuration in which the transcriptional and any translational regulatory elements are covalently attached to the encoding sequence in such disposition(s), relative to the coding sequence, that in and by action of the host cell, the regulatory elements can direct the expression of the coding sequence. Optionally the plasmid also encodes a fusion protein including an N-terminal identification polypeptide imparting desired characteristics, e.g., stabilization or simplified purification of expressed recombinant product, as discussed elsewhere herein.

Selectable Marker Gene

The plasmids described herein further comprise a selectable marker gene. This may be an antibiotic resistance gene(s), where the corresponding antibiotic(s) is added to the fermentation medium, or any other type of selection marker gene known in the art, e.g., a prototrophy-restoring gene where the plasmid is used in a host cell that is auxotrophic for the corresponding trait, e.g., a biocatalytic trait such as an amino acid biosynthesis or a nucleotide biosynthesis trait, or a carbon source utilization trait. Suitable selectable markers for use in the present invention include, but are not limited to: genes encoding ampicillin (Amp) resistance, kanamycin (Kan) resistance, tetracycline resistance, chloramphenicol resistance, and spectinomycin resistance. Also suitable as genetic markers are those genes encoding metal resistance, substrate-utilization, and genes encoding fluorescent and bioluminescent proteins (e.g., green fluorescent proteins, Lux genes), as well as lacZ, gfp, cat, galK, inaZ, luc, luxAB, bgaB, nptII, phoA, uidA and xylE. Other suitable bacterial and yeast markers may be found in Sambrook, J. et al., supra.

Promoter

In various embodiments, the plasmid comprises a promoter operably linked to the gene encoding the protein of interest. The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Common examples of non-lac-type promoters useful in expression systems according to the present invention include, e.g., those listed in Table 1.

TABLE 1

Examples of non-lac Promoters

| Promoter | Inducer |
|---|---|
| $P_R$ | High temperature |
| $P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (ASM Press, Washington, D.C.); H. Schweizer (2001) Vectors to express foreign genes and techniques to monitor gene expression for Pseudomonads, Current Opinion in Biotechnology, 12:439-

445; and R. Slater & R. Williams (2000) The Expression of Foreign DNA in Bacteria, in Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell may also be used to control expression of the gene of interest, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-function regulatory proteins, e.g., *E. coli* NagC protein. Many regulated-promoter/promoter-regulatory-protein pairs are known in the art.

Promoter regulatory proteins interact with an effector compound, i.e. a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

By way of example, where a lac family promoter is utilized, a lacI gene can also be present in the system. The lacI gene, which is (normally) a constitutively expressed gene, encodes the Lac repressor protein (LacI protein) which binds to the lac operator of these promoters. Thus, where a lac family promoter is utilized, the lacI gene can also be included and expressed in the expression system. In the case of the lac promoter family members, e.g., the tac promoter, the effector compound is an inducer, preferably a gratuitous inducer such as IPTG (isopropyl-D-1-thiogalactopyranoside, also called "isopropylthiogalactoside").

For expression of a protein or polypeptide of interest, any plant promoter may also be used. A promoter may be a plant RNA polymerase II promoter. Elements included in plant promoters can be a TATA box or Goldberg-Hogness box, typically positioned approximately 25 to 35 basepairs upstream (5') of the transcription initiation site, and the CCAAT box, located between 70 and 100 basepairs upstream. In plants, the CCAAT box may have a different consensus sequence than the functionally analogous sequence of mammalian promoters (Messing et al. (1983) In: *Genetic Engineering of Plants*, Kosuge et al., eds., pp. 211-227). In addition, virtually all promoters include additional upstream activating sequences or enhancers (Benoist and Chambon (1981) *Nature* 290:304-310; Gruss et al. (1981) *Proc. Nat. Acad. Sci.* 78:943-947; and Khoury and Gruss (1983) *Cell* 27:313-314) extending from around −100 bp to −1,000 bp or more upstream of the transcription initiation site.

Other Elements

In one embodiment, the plasmid further comprises a coding sequence for expression of a protein or polypeptide of interest, operably linked to a leader or secretion signal sequence. The recombinant proteins and polypeptides can be expressed from polynucleotides in which the polypeptide coding sequence is operably linked to the leader sequence and transcription and translation regulatory elements to form a functional gene from which the host cell can express the protein or polypeptide.

Gram-negative bacteria have evolved numerous systems for the active export of proteins across their dual membranes. These routes of secretion include, e.g.: the ABC (Type I) pathway, the Path/Fla (Type III) pathway, and the Path/Vir (Type IV) pathway for one-step translocation across both the plasma and outer membrane; the Sec (Type II), Tat, MscL, and Holins pathways for translocation across the plasma membrane; and the Sec-plus-fimbrial usher porin (FUP), Sec-plus-autotransporter (AT), Sec-plus-two partner secretion (TPS), Sec-plus-main terminal branch (MTB), and Tat-plus-MTB pathways for two-step translocation across the plasma and outer membranes. In one embodiment, the signal sequences useful in the methods of the invention comprise the Sec secretion system signal sequences. (see, Agarraberes and Dice (2001) *Biochim Biophys Acta.* 1513:1-24; Muller et al. (2001) *Prog Nucleic Acid Res Mol. Biol.* 66:107-157; U.S. Patent Application Nos. 60/887,476 and 60/887,486, filed Jan. 31, 2007, each of which is herein incorporated by reference in its entirety).

Other regulatory elements may be included in a plasmid. Such elements include, but are not limited to, for example, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" polypeptide coding sequences, which facilitates identification, separation, purification, and/or isolation of an expressed polypeptide.

In another embodiment, the plasmid further comprises a tag sequence adjacent to the coding sequence for the protein or polypeptide of interest (or adjacent to the leader or signal sequence if applicable). In one embodiment, this tag sequence allows for purification of the protein. The tag sequence can be an affinity tag, such as a hexa-histidine affinity tag. In another embodiment, the affinity tag can be a glutathione-S-transferase molecule. The tag can also be a fluorescent molecule, such as yellow-fluorescent protein (YFP) or green-fluorescent protein (GFP), or analogs of such fluorescent proteins. The tag can also be a portion of an antibody molecule, or a known antigen or ligand for a known binding partner useful for purification.

Host Cell

The improved copy number plasmids described herein are useful for the production of heterologous protein in a host cell of interest. In one embodiment, the host cell is a *Pseudomonas* host cell. The Pseudomonads system offers advantages for commercial expression of polypeptides and enzymes, in comparison with other bacterial expression systems. In particular, *P. fluorescens* has been identified as an advantageous expression system. *P. fluorescens* encompasses a group of common, nonpathogenic saprophytes that colonize soil, water and plant surface environments. Commercial enzymes derived from *P. fluorescens* have been used to reduce environmental contamination, as detergent additives, and for stereoselective hydrolysis. *P. fluorescens* is also used agriculturally to control pathogens. U.S. Pat. No. 4,695,462 describes the expression of recombinant bacterial proteins in *P. fluorescens*. Between 1985 and 2004, many companies capitalized on the agricultural use of *P. fluorescens* for the production of pesticidal, insecticidal, and nematocidal toxins, as well as on specific toxic sequences and genetic manipulation to enhance expression of these. See, for example, PCT Application Nos. WO 03/068926 and WO 03/068948; PCT publication No. WO 03/089455; PCT Application No. WO 04/005221; and, U.S. Patent Publication Number 20060008877.

In one embodiment, the host cell useful for the heterologous production of a protein or a polypeptide of interest using the improved copy number plasmid described herein can be selected from "Gram-negative Proteobacteria Subgroup 18." "Gram-negative Proteobacteria Subgroup 18" is defined as the group of all subspecies, varieties, strains, and other subspecial units of the species *Pseudomonas fluorescens*, including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* Pf0-1; *Pseudomonas fluorescens* Pf-5 (ATCC BAA-477); *Pseudomonas fluorescens* SBW25; and *Pseudomonas fluorescens* subsp. *cellulosa* (NCIMB 10462).

The host cell can be selected from "Gram-negative Proteobacteria Subgroup 19." "Gram-negative Proteobacteria Subgroup 19" is defined as the group of all strains of *Pseudomonas fluorescens* biotype A. A particularly preferred strain of this biotype is *P. fluorescens* strain MB101 (see U.S. Pat. No. 5,169,760 to Wilcox), and derivatives thereof. An example of a preferred derivative thereof is *P. fluorescens* strain MB214, constructed by inserting into the MB101 chromosomal asd (aspartate dehydrogenase gene) locus, a native *E. coli* PlacI-lacI-lacZYA construct (i.e. in which PlacZ was deleted).

Additional *P. fluorescens* strains that can be used in the present invention include *Pseudomonas fluorescens* Migula and *Pseudomonas fluorescens* Loitokitok, having the following ATCC designations: [NCIB 8286]; NRRL B-1244; NCIB 8865 strain CO1; NCIB 8866 strain CO$_2$; 1291 [ATCC 17458; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [EM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212. [PJ 832]; 215 [PJ 849]; 216 [PJ 885]; 267 [B-9]; 271 [B-1612]; 401 [C71A; IFO 15831; PJ 187]; NRRL B-3178 [4; IFO. 15841]; KY 8521; 3081; 30-21; [IFO 3081]; N; PYR; PW; D946-B83 [BU 2183; FERM-P 3328]; P-2563 [FERM-P 2894; IFO 13658]; IAM-1126 [43F]; M-1; A506 [A5-06]; A505 [A5-05-1]; A526 [A5-26]; B69; 72; NRRL B-4290; PMW6 [NCIB 11615]; SC 12936; Al [IFO 15839]; F 1847 [CDC-EB]; F 1848 [CDC 93]; NCIB 10586; P17; F-12; AmMS 257; PRA25; 6133D02; 6519E01; Ni; SC15208; BNL-WVC; NCTC 2583 [NCIB 8194]; H13; 1013 [ATCC 11251; CCEB 295]; IFO 3903; 1062; or Pf-5.

In one embodiment, the host cell can be any cell capable of producing a protein or polypeptide of interest, including a *P. fluorescens* cell as described above. The most commonly used systems to produce proteins or polypeptides of interest include certain bacterial cells, particularly *E. coli*, because of their relatively inexpensive growth requirements and potential capacity to produce protein in large batch cultures. Yeasts are also used to express biologically relevant proteins and polypeptides, particularly for research purposes. Systems include *Saccharomyces cerevisiae* or *Pichia pastoris*. These systems are well characterized, provide generally acceptable levels of total protein expression and are comparatively fast and inexpensive. Insect cell expression systems have also emerged as an alternative for expressing recombinant proteins in biologically active form. In some cases, correctly folded proteins that are post-translationally modified can be produced. Mammalian cell expression systems, such as Chinese hamster ovary cells, have also been used for the expression of proteins or polypeptides of interest. On a small scale, these expression systems are often effective. Certain biologics can be derived from proteins, particularly in animal or human health applications. In another embodiment, the host cell is a plant cell, including, but not limited to, a tobacco cell, corn, a cell from an *Arabidopsis* species, potato or rice cell. In another embodiment, a multicellular organism is analyzed or is modified in the process, including but not limited to a transgenic organism. Techniques for analyzing and/or modifying a multicellular organism are generally based on techniques described for modifying cells described below.

In another embodiment, the host cell can be a prokaryote such as a bacterial cell including, but not limited to an *Escherichia* or a *Pseudomonas* species. Typical bacterial cells are described, for example, in "Biological Diversity: Bacteria and Archaeans", a chapter of the On-Line Biology Book, provided by Dr M J Farabee of the Estrella Mountain Community College, Arizona, USA at the website www.emc-.maricotpa.edu/faculty/farabee/BIOBK/BioBookDiversity. In certain embodiments, the host cell can be a Pseudomonad cell, and can typically be a *P. fluorescens* cell. In other embodiments, the host cell can also be an *E. coli* cell. In another embodiment the host cell can be a eukaryotic cell, for example an insect cell, including but not limited to a cell from a *Spodoptera, Trichoplusia, Drosophila* or an *Estigmene* species, or a mammalian cell, including but not limited to a murine cell, a hamster cell, a monkey, a primate or a human cell.

In one embodiment, the host cell can be a member of any of the bacterial taxa. The cell can, for example, be a member of any species of eubacteria. The host can be a member of any one of the taxa: Acidobacteria, Actinobacteira, Aquificae, Bacteroidetes, Chlorobi, Chlamydiae, Choroflexi, Chrysiogenetes, Cyanobacteria, Deferribacteres, *Deinococcus*, Dictyoglomi, Fibrobacteres, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae, *Thermus* (Thermales), or Verrucomicrobia. In a embodiment of a eubacterial host cell, the cell can be a member of any species of eubacteria, excluding Cyanobacteria.

The bacterial host can also be a member of any species of Proteobacteria. A proteobacterial host cell can be a member of any one of the taxa Alphaproteobacteria, Betaproteobacteria, Gammaproteobacteria, Deltaproteobacteria, or Epsilonproteobacteria. In addition, the host can be a member of any one of the taxa Alphaproteobacteria, Betaproteobacteria, or Gammaproteobacteria, and a member of any species of Gammaproteobacteria.

In one embodiment of a Gamma Proteobacterial host, the host will be a member of any one of the taxa Aeromonadales, Alteromonadales, Enterobacteriales, Pseudomonadales, or Xanthomonadales; or a member of any species of the Enterobacteriales or Pseudomonadales. In one embodiment, the host cell can be of the order Enterobacteriales, the host cell will be a member of the family Enterobacteriaceae, or may be a member of any one of the genera *Erwinia, Escherichia,* or *Serratia*; or a member of the genus *Escherichia*. Where the host cell is of the order Pseudomonadales, the host cell may be a member of the family Pseudomonadaceae, including the genus *Pseudomonas*. Gamma Proteobacterial hosts include members of the species *Escherichia coli* and members of the species *Pseudomonas fluorescens*.

Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 2 presents these families and genera of organisms.

TABLE 2

Families and Genera Listed in the Part, "Gram-Negative Aerobic Rods and Cocci" (in Bergey (1974))

| | |
|---|---|
| Family I. Pseudomomonaceae | Gluconobacter |
| | Pseudomonas |
| | Xanthomonas |
| | Zoogloea |
| Family II. Azotobacteraceae | Azomonas |
| | Azotobacter |
| | Beijerinckia |
| | Derxia |
| Family III. Rhizobiaceae | Agrobacterium |
| | Rhizobium |
| Family IV. Methylomonadaceae | Methylococcus |
| | Methylomonas |
| Family V. Halobacteriaceae | Halobacterium |
| | Halococcus |
| Other Genera | Acetobacter |
| | Alcaligenes |
| | Bordetella |
| | Brucella |
| | Francisella |
| | Thermus |

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia,* and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens,* and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus*; 2) Pseudomonadaceae family bacteria of the genera *Cellvibrio, Oligella,* and *Teredinibacter*; 3) Rhizobiaceae family bacteria of the genera *Chelatobacter, Ensifer, Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina,* and *Methylosphaera*.

In another embodiment, the host cell is selected from "Gram-negative Proteobacteria Subgroup 2." "Gram-negative Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beyerinckia* (13); *Derxia* (2); *Brucella* (4); *Agrobacterium* (79); *Chelatobacter* (2); *Ensifer* (3); *Rhizobium* (144); *Sinorhizobium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera; Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); and *Oceanimonas* (4).

Exemplary host cell species of "Gram-negative Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophagaflava*

(ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); and *Oceanimonas doudoroffii* (ATCC 27123).

In another embodiment, the host cell is selected from "Gram-negative Proteobacteria Subgroup 3." "Gram-negative Proteobacteria Subgroup 3" is defined as the group of Proteobacteria of the following genera: *Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 4." "Gram-negative Proteobacteria Subgroup 4" is defined as the group of Proteobacteria of the following genera: *Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 5." "Gram-negative Proteobacteria Subgroup 5" is defined as the group of Proteobacteria of the following genera: *Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

The host cell can be selected from "Gram-negative Proteobacteria Subgroup 6." "Gram-negative Proteobacteria Subgroup 6" is defined as the group of Proteobacteria of the following genera: *Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 7." "Gram-negative Proteobacteria Subgroup 7" is defined as the group of Proteobacteria of the following genera: *Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 8." "Gram-negative Proteobacteria Subgroup 8" is defined as the group of Proteobacteria of the following genera: *Brevundimonas; Blastomonas; Sphingomonas; Burkholderia; Ralstonia; Acidovorax; Hydrogenophaga; Stenotrophomonas; Xanthomonas*; and *Oceanimonas*.

The host cell can be selected from "Gram-negative Proteobacteria Subgroup 9." "Gram-negative Proteobacteria Subgroup 9" is defined as the group of Proteobacteria of the following genera: *Brevundimonas; Burkholderia; Ralstonia; Acidovorax; Hydrogenophaga; Pseudomonas; Stenotrophomonas*; and *Oceanimonas*.

The host cell can be selected from "Gram-negative Proteobacteria Subgroup 10." "Gram-negative Proteobacteria Subgroup 10" is defined as the group of Proteobacteria of the following genera: *Burkholderia; Ralstonia; Pseudomonas; Stenotrophomonas*; and *Xanthomonas*.

The host cell can be selected from "Gram-negative Proteobacteria Subgroup 11." "Gram-negative Proteobacteria Subgroup 11" is defined as the group of Proteobacteria of the genera: *Pseudomonas; Stenotrophomonas*; and *Xanthomonas*. The host cell can be selected from "Gram-negative Proteobacteria Subgroup 12." "Gram-negative Proteobacteria Subgroup 12" is defined as the group of Proteobacteria of the following genera: *Burkholderia; Ralstonia; Pseudomonas*. The host cell can be selected from "Gram-negative Proteobacteria Subgroup 13." "Gram-negative Proteobacteria Subgroup 13" is defined as the group of Proteobacteria of the following genera: *Burkholderia; Ralstonia; Pseudomonas*; and *Xanthomonas*. The host cell can be selected from "Gram-negative Proteobacteria Subgroup 14." "Gram-negative Proteobacteria Subgroup 14" is defined as the group of Proteobacteria of the following genera: *Pseudomonas* and *Xanthomonas*. The host cell can be selected from "Gram-negative Proteobacteria Subgroup 15." "Gram-negative Proteobacteria Subgroup 15" is defined as the group of Proteobacteria of the genus *Pseudomonas*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas aspleni* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphisi* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis;*

*Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis;* and *Pseudomonas xiamenensis.*

The host cell can be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii;* and *Pseudomonas veronii.*

Other suitable hosts include those classified in other parts of the reference, such as Gram (+) Proteobacteria. In one embodiment, the host cell is an *E. coli*. The genome sequence for *E. coli* has been established for *E. coli* MG1655 (Blattner, et al. (1997) The complete genome sequence of *Escherichia coli* K-12, *Science* 277(5331): 1453-74) and DNA microarrays are available commercially for *E. coli* K12 (MWG Inc, High Point, N.C.). *E. coli* can be cultured in either a rich medium such as Luria-Bertani (LB) (10 g/L tryptone, 5 g/L NaCl, 5 g/L yeast extract) or a defined minimal medium such as M9 (6 g/L Na$_2$HPO$_4$, 3 g/L KH$_2$PO$_4$, 1 g/L NH$_4$Cl, 0.5 g/L NaCl, pH 7.4) with an appropriate carbon source such as 1% glucose. Routinely, an over night culture of *E. coli* cells is diluted and inoculated into fresh rich or minimal medium in either a shake flask or a fermentor and grown at 37° C.

A host can also be of mammalian origin, such as a cell derived from a mammal including any human or non-human mammal. Mammals can include, but are not limited to primates, monkeys, porcine, ovine, bovine, rodents, ungulates, pigs, swine, sheep, lambs, goats, cattle, deer, mules, horses, monkeys, apes, dogs, cats, rats, and mice.

A host cell may also be of plant origin. Examples of suitable host cells would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. In some embodiments, plants useful in the method are *Arabidopsis*, corn, wheat, soybean, and cotton.

Methods

Also provided herein are methods for generating plasmids with improved copy number. The methods of the present invention involve the reiterative selection of improved copy number plasmids by: (a) introducing a control plasmid comprising a gene conferring resistance to a selection agent into a host cell, wherein the control plasmid is capable of replicating in the host cell; (b) growing the host cell comprising the control plasmid in the presence of an amount of the selection agent that is sufficient to inhibit the growth of a host cell not containing the control plasmid; (c) selecting one or more populations of host cells capable of growth under these conditions; (d) growing one or more of the selected populations of host cells in the presence of the selection agent at an amount that is higher than the amount used in the previous selection step; (e) measuring the copy number of the plasmid in one or more populations of host cells capable of growth under the higher amount of the selection agent; and, (f) selecting a host cell population comprising a plasmid that has a copy number that is higher than the copy number of the control plasmid. The steps of growth and selection can be sequentially repeated using higher amounts of the selection agent.

In one embodiment, the control plasmid comprises a gene conferring resistance to an antibiotic selection agent, and the selection agent applied to the host cells is that antibiotic. Correlation between gene copy number and antibiotic resistance level has been well established (Cabello et al., 1976; Uhlin and Nordstrom, 1977). This correlation has been employed to select for high kanamycin resistance gene copy number transformants of *Pichia pastoris* using high concentrations of the antibiotic G418 (Scorer et al., 1994). Spontaneous mutations arise as natural errors in DNA replication at frequencies ranging from $10^{-4}$ to $10^{-11}$ mutations per base pair (Drake et al., 1998). These mutations occur randomly either on the chromosome or any plasmid present in the cell.

The amount of a selection agent that is sufficient to inhibit the growth of a host cell not containing the control plasmid can be determined empirically by methods known in the art. The amount of selection agent that is used in each subsequent growth and selection step is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, or more than the amount of selection agent used in the previous growth and selection step. Alternatively, the amount of selection agent that is used in each subsequent growth and selection step is at least about 2-fold, at least about 3-fold, at least about 4-fold, at least about 5-fold, at least about 10-fold, at least about 15-fold, at least about 20-fold, or greater than the amount of selection agent used in the previous growth and selection step.

In various aspects of the invention, the control plasmid comprises a *Pseudomonas*-specific replication control region. In some embodiments, the replication control region encodes a RepA protein. For example, the control plasmid may comprise the repA sequence set forth in SEQ ID NO:1 or a nucleotide sequence encoding the RepA protein set forth in SEQ ID NO:2. The control plasmid may contain additional elements to facilitate replication in other organisms, such as the replication control region found in the pBR22 family of plasmids, or ColE1 derived plasmids. Additional control plasmids useful in the invention include RSF1010 based plasmids such as pKT262 and pPS10 based plasmids such as pCN38. The copy numbers of these plasmids are approximately 15-20 copies per cell (Bagdasarian and Timmis, *Curr. Topics Microbiol. Immunol.* (1981) 47-67; Nieto et al., *Gene* 87 (1990) 145-149). It is contemplated that any plasmid capable of replication in a host cell may be used in the methods described herein to generate an improved copy number plasmid, so long as the plasmid comprises a gene conferring resistance to a selection agent as discussed supra.

The improved copy number plasmids generated by the methods disclosed herein have a copy number that is at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 65-fold, at least about 70-fold, at least about 75-fold, at least about 80-fold, at least about 85-fold, at least about 90-fold, at least about 95-fold, at least about 100-fold, at least about 110-fold, at least about 120-fold, or greater than the control plasmid from which it was derived. In one embodiment, the copy number of the control plasmid is at least about 5 copies per cell, at least about 10 copies per cell, at least about 15, at least about 20, at least about 25, at least about 30, at least about 35, at least about 40, at least about 45, or at least about 50 copies per cell, and the improved copy number plasmid has a copy number of at least about 55 copies per cell, at least about 60 copies per cell, at least about 65, at least about 70, at least about 75, at least about 80, at least about 85, at least about 90, at least about 95, or at least about 100 copies per cell, at least about 150, at least about 200, at least about 250, at least about 300, at least about 350, at least about 400, at least about 450, at least about 500, or more copies per cell. Methods for determining copy number are described elsewhere herein.

In various embodiments encompassed herein, it is desirable to generate and utilize a very high copy number plasmid. It should be noted, however, that the preferred range for optimal gene expression for any given host cell may be an intermediate copy number range (e.g., 50-100 copies per cell) so as to provide the adequate gene dosage effect for optimal rate or final level of expression, while keeping to a minimum leaky expression of the gene product, usually associated with higher copy number plasmids, which can cause poor growth, plasmid instability and overall expression. Intermediate copy number plasmids can be generated by the methods disclosed herein.

The improved copy number plasmid can also be selected based on the production of an increased level of recoverable protein or polypeptide produced per gram of recombinant or per gram of host cell. The improved copy number plasmid may also be selected based on the production of an increased level of properly processed protein or polypeptide per gram of protein produced, or per gram of host protein. The plasmids may be selected based on any combination of an increased expression, increased activity, increased solubility, or increased translocation (e.g., to a periplasmic compartment or secreted into the extracellular space). In this embodiment, the term "increased" is relative to the level of protein or polypeptide that is recoverable, produced, properly processed, and/or soluble when the protein or polypeptide of interest is expressed under the same conditions using a control plasmid. The improved copy number plasmids can lead to an increase in the production of protein or polypeptide that is recoverable, properly processed and/or soluble of at least about 5%, at least about 10%, at least about 15%, at least about 20%, about 25%, about 30%, about 35%, about 40%, about 45%, about 50%, about 55%, about 60%, about 65%, about 70, at least about 75% or more, or at least about 2-fold, about 3-fold, about 4-fold, about 5-fold, about 6-fold, about 7-fold, about 10-fold, about 20-fold, or greater.

Other Mutagenesis Procedures

Mutations in the control plasmid can also be introduced by other random or targeted mutagenesis procedures to generate the improved copy number plasmids described herein. Various methods are known for mutating a wild-type nucleotide sequence to produce a mutated product with altered activity including, but not limited to: 1.) error-prone PCR (Leung et al., Techniques, 1:11-15 (1989); Zhou et al., Nucleic Acids Res., 19:6052-6052 (1991); Spee et al., Nucleic Acids Res., 21:777-778 (1993); Melnikov et al., Nucleic Acids Research, 27(4):1056-1062 (Feb. 15, 1999)); 2.) site directed mutagenesis (Coombs et al., Proteins, 259-311, 1 plate. Ed.: Angeletti, Ruth Hogue. Academic: San Diego, Calif. (1998)); 3.) in vivo mutagenesis; and 4.) "gene shuffling" (U.S. Pat. No. 5,605,793; U.S. Pat. No. 5,811,238; U.S. Pat. No. 5,830,721; and U.S. Pat. No. 5,837,458, hereby incorporated by reference).

Error-prone PCR is a particularly preferred method for the generation of mutations within a defined nucleotide sequence. The principal advantage of error-prone PCR is that all mutations introduced by this method will be within a defined region, and any change may be easily controlled by changing the PCR conditions. Alternatively, in vivo mutagenesis may be employed using commercially available materials such as the *E. coli* XL1-Red strain or the Epicurian® coli XL1-Red mutator strain (Stratagene, La Jolla, Calif.; Greener and Callahan, Strategies, 7:32-34 (1994)). This latter strain is deficient in three of the primary DNA repair pathways (i.e., mutS, mutD, and mutT), resulting in a mutation rate 5000-fold higher than that of wild type. In vivo mutagenesis does not depend on ligation efficiency (as with error-prone PCR); however, a mutation may occur at any region of the plasmid and the mutation rates are generally much lower.

Alternatively, it is contemplated that an improved copy number plasmid may be constructed using the method of "gene shuffling". The method of gene shuffling is particularly attractive due to its facile implementation, and high rate of mutagenesis and ease of screening. The process of gene shuffling involves the restriction endonuclease cleavage of a nucleotide sequence (e.g., a gene) of interest into fragments of specific size in the presence of additional populations of DNA regions of both similarity to (or difference to) the sequence of interest. This pool of fragments will then be denatured and reannealed to create a mutated sequence within the plasmid. The mutated sequence is then screened for improved copy number.

Screening for Improved Copy Number Plasmids

Host cell populations suspected of containing an improved copy number plasmid can be screened by measuring the copy number or by measuring the level of expression of a heterologous gene encoded by the plasmid. Plasmid copy number can be determined using a number of different methods, including measuring the absolute or the relative copy number. One method to determine the relative copy number of plasmids is described in U.S. Pat. No. 4,703,012. In this method, control plasmids are grown in parallel with test plasmids (e.g., candidate improved copy number plasmids). The cells are lysed, and the plasmids are compared by agarose gel electrophoresis at various dilutions. If the test plasmid stains more intensely with ethidium bromide at a given dilution compared to the control plasmid, then its copy number is increased by an amount proportional to the increase in staining.

Alternatively, plasmid copy number can be determined as a proportion of chromosome copies. In this method, bacterial cells are lysed, protein is digested by a protease, and total DNA is analyzed by agarose gel electrophoresis. The relative amounts of plasmid to chromosomal DNA can be determined for a control plasmid, and compared to a test plasmid. This comparison can be quantified using ethidium bromide staining of the agarose gels.

The absolute copy number of a plasmid within a cell can be determined by analyzing the average number of plasmid molecules within a cell in a given host cell population. In this method, a population of cells containing the test plasmid is grown, and an aliquot of cells are lysed in mid log phase. Plasmid DNA is prepared from this aliquot by any of several standard techniques. The plasmid DNA concentration, and absolute amount, are determined by spectroscopy or fluorometry. The remaining cells are then plated in multiple dilutions on LB plates with the appropriate antibiotic selection. The colonies growing on these plates are then counted to give an accurate measure of the viable cells in the original culture. The copy number is then determined by deducing the number of copies/viable cell using the data acquired in the aforementioned process. Alternatively, the optical density of a bacterial colony often relates linearly to its cell count. Hence, optical density can be used as the denominator of the preceding calculation.

Under some circumstances, preliminary screening for improved plasmid copy number may be facile, for example, when the mutant replication control region is present within a plasmid comprising a reporter gene(s) and wherein the plasmid is expressed within a particular host. Thus, cells containing the mutagenized replication control region may be selected based on the ability to detect the over-expression or under-expression of the reporter (either directly or indirectly, by visual means or other techniques). For example, the reporter protein may be expressed alone or as a fusion to another protein. And, the reporter protein can be detected by, for example: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product), or 2.) its light-producing or modifying characteristics (e.g., the green fluorescent protein of *Aequorea Victoria* fluoresces when illuminated with blue light). Using these means, the over-expression of the reporter is indicative of an improved copy number plasmid.

Where more quantitative means are desired to detect improved plasmid copy number, it is useful to quantify plasmid DNA in the cell. One suitable method is the use of real-time PCR (for a general review of real-time PCR applications, see Ginzinger, D. J., Experimental Hematology, 30:503-512 (2002)). Real-time PCR is based on the detection and quantitation of a fluorescent reporter. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. There are two general methods for the quantitative detection of the amplicon: (1) use of fluorescent probes; or (2) use of DNA-binding agents (e.g., SYBR-green I or ethidium bromide). For relative gene expression comparisons, it is necessary to use an endogenous control as an internal reference (e.g., the chromosomally encoded 16S rRNA gene), thereby allowing one to normalize for differences in the amount of total DNA added to each real-time PCR reaction. Specific methods for real-time PCR are well documented in the art. See, for example, the Real Time PCR Special Issue (Methods, 25(4):383-481 (2001)).

Following a real-time PCR reaction, the recorded fluorescence intensity is used to quantitate the amount of template by use of: 1.) an absolute standard method (wherein a known amount of standard such as in vitro translated RNA (cRNA) is used); 2.) a relative standard method (wherein known amounts of the target nucleic acid are included in the assay design in each run); or 3.) a comparative $C_T$ method ($\Delta\Delta C_T$) for relative quantitation of gene expression (wherein the relative amount of the target sequence is compared to any of the reference values chosen and the result is given as relative to the reference value).

A host cell comprising a test plasmid can also be screened for the presence of an improved copy number plasmid by measuring the level of expression of a heterologous protein of interest encoded by the plasmid. The improved copy number plasmid can be identified or selected based on the quantity, quality, and/or location of the expressed protein of interest. In one embodiment, the improved copy number plasmid is one that results in an increased level of total protein, increased level of properly processed protein, or increased level of active or soluble protein within (or secreted from) the host cell comprising the improved copy number plasmid compared to a host cell comprising a parental or control plasmid.

An increased expression level of a protein or polypeptide of interest can refer to an increase in the solubility of the protein. The protein or polypeptide of interest can be produced and recovered from the cytoplasm, periplasm or extracellular medium of the host cell. The protein or polypeptide can include one or more targeting sequences or sequences to assist purification, as discussed supra.

The term "soluble" as used herein means that the protein is not precipitated by centrifugation at between approximately 5,000 and 20,000× gravity when spun for 10-30 minutes in a buffer under physiological conditions. Soluble proteins are not part of an inclusion body or other precipitated mass. Similarly, "insoluble" means that the protein or polypeptide can be precipitated by centrifugation at between 5,000 and 20,000× gravity when spun for 10-30 minutes in a buffer under physiological conditions. Insoluble proteins or polypeptides can be part of an inclusion body or other precipitated mass. The term "inclusion body" is meant to include any intracellular body contained within a cell wherein an aggregate of proteins or polypeptides has been sequestered. In some embodiments, expression of a gene from an improved copy number plasmid results in a decrease in the accumulation of insoluble protein in inclusion bodies. The decrease in accumulation may be a decrease of at least about 5%, at least about 10%, at least about 15%, at least about 20%, about 25%, about 30%, about 35%, about 40%, about 45%, about 50%, about 55%, about 60%, about 65%, about 70, at least about 75% or more, or at least about 2-fold, about 3-fold, about 4-fold, about 5-fold, about 6-fold, about 7-fold, or greater.

The methods of the invention can produce protein localized to the periplasm of the host cell. In one embodiment, the improved copy number plasmid results in an increase in the production of properly processed proteins or polypeptides of interest in the cell. In another embodiment, there may be an increase in the production of active proteins or polypeptides of interest in the cell. The improved copy number plasmid may also lead to an increased yield of active and/or soluble proteins or polypeptides of interest as compared to when the protein is expressed from a parental or control plasmid.

In one embodiment, the improved copy number plasmid results in the production of at least 0.1 g/L protein in the periplasmic compartment. In another embodiment, the improved copy number plasmid results in the production of 0.1 to 10 g/L periplasmic protein in the cell, or at least about 0.2, about 0.3, about 0.4, about 0.5, about 0.6, about 0.7, about 0.8, about 0.9 or at least about 1.0 g/L periplasmic protein. In one embodiment, the total protein or polypeptide of interest produced is at least 1.0 g/L, at least about 2 g/L, at least about 3 g/L, about 4 g/L, about 5 g/L, about 6 g/L, about 7 g/L, about 8 g/L, about 10 g/L, about 15 g/L, about 20 g/L, at least about 25 g/L, or greater. In some embodiments, the amount of periplasmic protein produced is at least about 5%, about 10%, about 15%, about 20%, about 25%, about 30%, about 40%, about 50%, about 60%, about 70%, about 80%, about 90%, about 95%, about 96%, about 97%, about 98%, about 99%, or more of total protein or polypeptide of interest produced.

In one embodiment, the improved copy number plasmid results in the production of at least 0.1 g/L correctly processed protein. A correctly processed protein has an amino terminus of the native protein. In another embodiment, the improved copy number plasmid results in the production of 0.1 to 10 g/L correctly processed protein in the cell, including at least about 0.2, about 0.3, about 0.4, about 0.5, about 0.6, about 0.7, about 0.8, about 0.9 or at least about 1.0 g/L correctly processed protein. In another embodiment, the total correctly processed protein or polypeptide of interest produced is at least 1.0 g/L, at least about 2 g/L, at least about 3 g/L, about 4 g/L, about 5 g/L, about 6 g/L, about 7 g/L, about 8 g/L, about 10 g/L, about 15 g/L, about 20 g/L, about 25 g/L, about 30 g/L, about 35 g/l, about 40 g/l, about 45 g/l, at least about 50 g/L, or greater. In some embodiments, the amount of correctly processed protein produced is at least about 5%, about 10%, about 15%, about 20%, about 25%, about 30%, about 40%, about 50%, about 60%, about 70%, about 80%, about 90%, about 95%, about 96%, about 97%, about 98%, at least about 99%, or more of total recombinant protein in a correctly processed form.

The improved copy number plasmid can also be screened based on the production of an increased yield of the protein or polypeptide of interest. In one embodiment, the improved plasmid results in the production of a protein or polypeptide of interest as at least about 5%, at least about 10%, about 15%, about 20%, about 25%, about 30%, about 40%, about 45%, about 50%, about 55%, about 60%, about 65%, about 70%, about 75%, or greater of total cell protein (tcp). "Percent total cell protein" is the amount of protein or polypeptide in the host cell as a percentage of aggregate cellular protein. The determination of the percent total cell protein is well known in the art.

In a particular embodiment, the host cell comprising the improved copy number plasmid can have a recombinant polypeptide, polypeptide, protein, or fragment thereof expression level of at least 1% tcp and a cell density of at least 40 g/L, when grown (i.e. within a temperature range of about 4° C. to about 55° C., including about 10° C., about 15° C., about 20° C., about 25° C., about 30° C., about 35° C., about 40° C., about 45° C., and about 50° C.) in a mineral salts medium. In a particularly preferred embodiment, the optimal expression system will have a protein or polypeptide expression level of at least 5% tcp and a cell density of at least 40 g/L, when grown (i.e. within a temperature range of about 4° C. to about 55° C., inclusive) in a mineral salts medium at a fermentation scale of at least about 10 Liters.

In practice, heterologous proteins targeted to the periplasm are often found in the broth (see European Patent No. EP 0 288 451), possibly because of damage to or an increase in the fluidity of the outer cell membrane. The rate of this "passive" secretion may be increased by using a variety of mechanisms that permeabilize the outer cell membrane: colicin (Miksch et al. (1997) *Arch. Microbiol.* 167: 143-150); growth rate (Shokri et al. (2002) *App Miocrobiol Biotechnol* 58:386-392); TolIII overexpression (Wan and Baneyx (1998) *Protein Expression Purif.* 14: 13-22); bacteriocin release protein (Hsiung et al. (1989) *Bio/Technology* 7: 267-71), colicin A lysis protein (Lloubes et al. (1993) *Biochimie* 75: 451-8) mutants that leak periplasmic proteins (Furlong and Sundstrom (1989) Developments in Indus. *Microbio.* 30: 141-8); fusion partners (Jeong and Lee (2002) *Appl. Environ. Microbio.* 68: 4979-4985); recovery by osmotic shock (Taguchi et al. (1990) *Biochimica Biophysica Acta* 1049: 278-85). Transport of engineered proteins to the periplasmic space with subsequent localization in the broth has been used to produce properly folded and active proteins in *E. coli* (Wan and Baneyx (1998) *Protein Expression Purif.* 14: 13-22; Simmons et al. (2002) *J. Immun. Meth.* 263: 133-147; Lundell et al. (1990) *J. Indust. Microbio.* 5: 215-27).

In some embodiments, the methods of the invention generate an improved copy number plasmid that results in an increase in the amount of protein produced in an active form. The term "active" means the presence of biological activity, wherein the biological activity is comparable or substantially corresponds to the biological activity of a corresponding native protein or polypeptide. In the context of proteins this typically means that a polynucleotide or polypeptide comprises a biological function or effect that has at least about 20%, about 50%, preferably at least about 60-80%, and most preferably at least about 90-95% activity compared to the corresponding native protein or polypeptide using standard parameters. The determination of protein or polypeptide activity can be performed utilizing corresponding standard, targeted comparative biological assays for particular proteins or polypeptides. One indication that a protein or polypeptide of interest maintains biological activity is that the polypeptide is immunologically cross reactive with the native polypeptide.

The improved copy number plasmid of the invention can also improve recovery of active protein or polypeptide of interest. Active proteins can have a specific activity of at least about 20%, at least about 30%, at least about 40%, about 50%, about 60%, at least about 70%, about 80%, about 90%, or at least about 95% that of the native protein or polypeptide from which the sequence is derived. Further, the substrate specificity ($k_{cat}/K_m$) is optionally substantially similar to the native protein or polypeptide. Typically, $k_{cat}/K_m$ will be at least about 30%, about 40%, about 50%, about 60%, about 70%, about 80%, at least about 90%, at least about 95%, or greater. Methods of assaying and quantifying measures of protein and polypeptide activity and substrate specificity ($k_{cat}/K_m$), are well known to those of skill in the art.

The activity of the protein or polypeptide of interest can be also compared with a previously established native protein or polypeptide standard activity. Alternatively, the activity of the protein or polypeptide of interest can be determined in a simultaneous, or substantially simultaneous, comparative assay with the native protein or polypeptide. For example, in vitro assays can be used to determine any detectable interaction between a protein or polypeptide of interest and a target, e.g. between an expressed enzyme and substrate, between expressed hormone and hormone receptor, between expressed antibody and antigen, etc. Such detection can include the measurement of calorimetric changes, proliferation changes, cell death, cell repelling, changes in radioactivity, changes in solubility, changes in molecular weight as measured by gel electrophoresis and/or gel exclusion methods, phosphorylation abilities, antibody specificity assays such as ELISA assays, etc. In addition, in vivo assays include, but are not limited to, assays to detect physiological effects of the heterologously produced protein or polypeptide in comparison to physiological effects of the native protein or polypeptide, e.g. weight gain, change in electrolyte balance, change in blood clotting time, changes in clot dissolution and the induction of antigenic response. Generally, any in vitro or in vivo assay can be used to determine the active nature of the protein or polypeptide of interest that allows for a comparative analysis to the native protein or polypeptide so long as such activity is assayable. Alternatively, the proteins or polypeptides produced in the present invention can be assayed for the ability to stimulate or inhibit interaction between the protein or polypeptide and a molecule that normally interacts with the protein or polypeptide, e.g. a substrate or a component of the signal pathway that the native protein normally interacts. Such assays can typically include the steps of combining the protein with a substrate molecule under conditions that allow the protein or polypeptide to interact with the target molecule, and detect the biochemical consequence of the interaction with the protein and the target molecule.

Assays that can be utilized to determine protein or polypeptide activity are described, for example, in Ralph, P. J., et al. (1984) *J. Immunol.* 132:1858 or Saiki et al. (1981) *J. Immunol.* 127:1044, Steward, W. E. II (1980) *The Interferon Systems.* Springer-Verlag, Vienna and New York, Broxmeyer, H. E., et al. (1982) *Blood* 60:595, *Molecular Cloning: A Laboratory Manua"*, 2d ed., Cold Spring Harbor Laboratory Press, Sambrook, J., E. F. Fritsch and T. Maniatis eds., 1989, and *Methods in Enzymology: Guide to Molecular Cloning Techniques*, Academic Press, Berger, S. L. and A. R. Kimmel eds., 1987, A K Patra et al., *Protein Expr Purif,* 18(2): p/182-92 (2000), Kodama et al., *J. Biochem.* 99: 1465-1472 (1986); Stewart et al., *Proc. Natl. Acad. Sci.* USA 90: 5209-5213 (1993); (Lombillo et al., *J. Cell Biol.* 128:107-115 (1995); (Vale et al., *Cell* 42:39-50 (1985).

Isolation of Protein or Polypeptide of Interest

It may be desirable to isolate the proteins produced using the methods and compositions of this invention. These proteins may be isolated and purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused with a ligand. With the appropriate ligand, the protein can be selectively adsorbed to a purification column and then freed from the column in a relatively pure form. The fused protein is then removed by enzymatic activity. In addition, protein can be purified using immunoaffinity columns or Ni-NTA columns. General techniques are further described in, for example, R. Scopes, Protein Purification: Principles and Practice, Springer-Verlag: N.Y. (1982); Deutscher, Guide to Protein Purification, Academic Press (1990); U.S. Pat. No. 4,511,503; S. Roe, Protein Purification Techniques: A Practical Approach (Practical Approach Series), Oxford Press (2001); D. Bollag, et al., Protein Methods, Wiley-Lisa, Inc. (1996); A K Patra et al., Protein Expr Purif, 18(2): p/182-92 (2000); and R. Mukhija, et al., Gene 165(2): p. 303-6 (1995). See also, for example, Ausubel, et al. (1987 and periodic supplements); Deutscher (1990) "Guide to Protein Purification," Methods in Enzymology vol. 182, and other volumes in this series; Coligan, et al. (1996 and periodic Supplements) Current Protocols in Protein Science Wiley/Greene, N.Y.; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example, Hochuli (1989) Chemische Industrie 12:69-70; Hochuli (1990) "Purification of Recombinant Proteins with Metal Chelate Absorbent" in Setlow (ed.) Genetic Engineering, Principle and Methods 12:87-98, Plenum Press, NY; and Crowe, et al. (1992) QIAexpress: The High Level Expression & Protein Purification System QUIAGEN, Inc., Chatsworth, Calif.

An initial salt fractionation can separate many of the unwanted host cell proteins (or proteins derived from the cell culture media) from the protein or polypeptide of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a protein or polypeptide of interest can also be used to isolated it from proteins of greater and lesser size using ultrafiltration through membranes of different pore size (for example, Amicon or Millipore membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The protein or polypeptide of interest will pass through the membrane into the filtrate. The filtrate can then be chromatographed as described below.

The secreted proteins or polypeptides of interest can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Conventional methods for the recovery of proteins or polypeptides of interest from the cytoplasm, as soluble protein or refractile particles, involved disintegration of the bacterial cell by mechanical breakage. Mechanical disruption typically involves the generation of local cavitation in a liquid suspension, rapid agitation with rigid beads, sonication, or grinding of cell suspension (Bacterial Cell Surface Techniques, Hancock and Poxton (John Wiley & Sons Ltd, 1988), Chapter 3, p. 55).

HEW-lysozyme acts biochemically to hydrolyze the peptidoglycan backbone of the cell wall. The method was first developed by Zinder and Arndt (1956) Proc. Natl. Acad. Sci. USA, 42: 586-590, who treated E. coli with egg albumin (which contains HEW-lysozyme) to produce rounded cellular spheres later known as spheroplasts. These structures retained some cell-wall components but had large surface areas in which the cytoplasmic membrane was exposed. U.S. Pat. No. 5,169,772 discloses a method for purifying heparinase from bacteria comprising disrupting the envelope of the bacteria in an osmotically-stabilized medium, e.g., 20% sucrose solution using, e.g., EDTA, lysozyme, or an organic compound, releasing the non-heparinase-like proteins from the periplasmic space of the disrupted bacteria by exposing the bacteria to a low-ionic-strength buffer, and releasing the heparinase-like proteins by exposing the low-ionic-strength-washed bacteria to a buffered salt solution.

Alternatively, it is possible to purify the proteins or polypeptides of interest from the host periplasm. After lysis of the host cell, when the protein is exported into the periplasm of the host cell, the periplasmic fraction of the bacteria can be isolated by cold osmotic shock in addition to other methods known to those skilled in the art. To isolate targeted proteins from the periplasm, for example, the bacterial cells can be centrifuged to form a pellet. The pellet can be resuspended in a buffer containing 20% sucrose. To lyse the cells, the bacteria can be centrifuged and the pellet can be resuspended in ice-cold 5 mM MgSO4 and kept in an ice bath for approximately 10 minutes. The cell suspension can be centrifuged and the supernatant decanted and saved. The targeted proteins present in the supernatant can be separated from the host proteins by standard separation techniques well known to those of skill in the art.

To release targeted proteins from the periplasm, treatments involving chemicals such as chloroform (Ames et al. (1984) J. Bacteriol., 160: 1181-1183), guanidine-HCl, and Triton X-100 (Naglak and Wang (1990) Enzyme Microb. Technol., 12: 603-611) have been used. However, these chemicals are not inert and may have detrimental effects on many recombinant protein products or subsequent purification procedures. Glycine treatment of E. coli cells, causing permeabilization of the outer membrane, has also been reported to release the periplasmic contents (Ariga et al. (1989) J. Ferm. Bioeng., 68: 243-246). The most widely used methods of periplasmic release of recombinant protein are osmotic shock (Nosal and Heppel (1966) J. Biol. Chem., 241: 3055-3062; Neu and Heppel (1965) J. Biol. Chem., 240: 3685-3692), hen eggwhite (HEW)-lysozyme/ethylenediamine tetraacetic acid (EDTA) treatment (Neu and Heppel (1964) J. Biol. Chem., 239: 3893-3900; Witholt et al. (1976) Biochim. Biophys. Acta, 443: 534-544; Pierce et al. (1995) ICheme Research. Event, 2: 995-997), and combined HEW-lysozyme/osmotic shock treatment (French et al. (1996) Enzyme and Microb. Tech., 19: 332-338). The French method involves resuspension of the cells in a fractionation buffer followed by recovery of the periplasmic fraction, where osmotic shock immediately follows lysozyme treatment.

Typically, these procedures include an initial disruption in osmotically-stabilizing medium followed by selective release in non-stabilizing medium. The composition of these media (pH, protective agent) and the disruption methods used (chloroform, HEW-lysozyme, EDTA, sonication) vary among specific procedures reported. A variation on the HEW-lysozyme/EDTA treatment using a dipolar ionic detergent in place of EDTA is discussed by Stabel et al. (1994) Veterinary Microbiol., 38: 307-314. For a general review of use of intracellular lytic enzyme systems to disrupt E. coli, see Dabora and Cooney (1990) in Advances in Biochemical Engineering/Biotechnology, Vol. 43, A. Fiechter, ed. (Springer-Verlag: Berlin), pp. 11-30.

Many different modifications of these methods have been used on a wide range of expression systems with varying degrees of success (Joseph-Liazun et al. (1990) Gene, 86: 291-295; Carter et al. (1992) Bio/Technology, 10: 163-167). Efforts to induce recombinant cell culture to produce lysozyme have been reported. EP 0 155 189 discloses a means for inducing a recombinant cell culture to produce lysozymes, which would ordinarily be expected to kill such host cells by means of destroying or lysing the cell wall structure.

U.S. Pat. No. 4,595,658 discloses a method for facilitating externalization of proteins transported to the periplasmic space of E. coli. This method allows selective isolation of proteins that locate in the periplasm without the need for lysozyme treatment, mechanical grinding, or osmotic shock treatment of cells. U.S. Pat. No. 4,637,980 discloses producing a bacterial product by transforming a temperature-sensitive lysogen with a DNA molecule that codes, directly or indirectly, for the product, culturing the transformant under permissive conditions to express the gene product intracellularly, and externalizing the product by raising the temperature to induce phage-encoded functions. Asami et al. (1997) J. Ferment. and Bioeng., 83: 511-516 discloses synchronized disruption of E. coli cells by T4 phage infection, and Tanji et al. (1998) J. Ferment. and Bioeng., 85: 74-78 discloses controlled expression of lysis genes encoded in T4 phage for the gentle disruption of E. coli cells.

Detection of the expressed protein is achieved by methods known in the art and include, for example, radioimmunoassays, Western blotting techniques or immunoprecipitation.

Cell Growth Conditions

The cell growth conditions for the host cells described herein can include that which facilitates replication of the plasmid described herein, expression of the protein of interest from the plasmid, and/or that which facilitates fermentation of the expressed protein of interest. As used herein, the term "fermentation" includes both embodiments in which literal fermentation is employed and embodiments in which other, non-fermentative culture modes are employed. Fermentation may be performed at any scale. In one embodiment, the fermentation medium may be selected from among rich media, minimal media, and mineral salts media; a rich medium may be used, but is preferably avoided. In another embodiment either a minimal medium or a mineral salts medium is selected. In still another embodiment, a minimal medium is selected. In yet another embodiment, a mineral salts medium is selected. Mineral salts media are particularly preferred.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli (1950) in *J. Bact.* 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. The mineral salts medium does not have, but can include an organic nitrogen source, such as peptone, tryptone, amino acids, or a yeast extract. An inorganic nitrogen source can also be used and selected from among, e.g., ammonium salts, aqueous ammonia, and gaseous ammonia. In comparison to mineral salts media, minimal media can also contain mineral salts and a carbon source, but can be supplemented with, e.g., low levels of amino acids, vitamins, peptones, or other ingredients, though these are added at very minimal levels.

The expression system according to the present invention can be cultured in any fermentation format. For example, batch, fed-batch, semi-continuous, and continuous fermentation modes may be employed herein. Wherein the protein is excreted into the extracellular medium, continuous fermentation is preferred.

The expression systems according to the present invention are useful for transgene expression at any scale (i.e. volume) of fermentation. Thus, e.g., microliter-scale, centiliter scale, and deciliter scale fermentation volumes may be used; and 1 Liter scale and larger fermentation volumes can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters or 50,000 Liters.

In the present invention, growth, culturing, and/or fermentation of the transformed host cells is performed within a temperature range permitting survival of the host cells, preferably a temperature within the range of about 4° C. to about 55° C., inclusive. Thus, e.g., the terms "growth" (and "grow," "growing"), "culturing" (and "culture"), and "fermentation" (and "ferment," "fermenting"), as used herein in regard to the host cells of the present invention, inherently means "growth," "culturing," and "fermentation," within a temperature range of about 4° C. to about 55° C., inclusive. In addition, "growth" is used to indicate both biological states of active cell division and/or enlargement, as well as biological states in which a non-dividing and/or non-enlarging cell is being metabolically sustained, the latter use of the term "growth" being synonymous with the term "maintenance."

In some embodiments, the expression system comprises a *Pseudomonas* host cell, e.g. *Pseudomonas fluorescens*. An advantage in using *Pseudomonas fluorescens* in expressing secreted proteins includes the ability of *Pseudomonas fluorescens* to be grown in high cell densities compared to *E. coli* or other bacterial expression systems. To this end, *Pseudomonas fluorescens* expressions systems according to the present invention can provide a cell density of about 20 g/L or more.

The *Pseudomonas fluorescens* expressions systems according to the present invention can likewise provide a cell density of at least about 70 g/L, as stated in terms of biomass per volume, the biomass being measured as dry cell weight.

In one embodiment, the cell density will be at least about 20 g/L. In another embodiment, the cell density will be at least about 25 g/L, about 30 g/L, about 35 g/L, about 40 g/L, about 45 g/L, about 50 g/L, about 60 g/L, about 70 g/L, about 80 g/L, about 90 g/L, about 100 g/L, about 110 g/L, about 120 g/L, about 130 g/L, about 140 g/L, about or at least about 150 g/L.

In another embodiments, the cell density at induction will be between about 20 g/L and about 150 g/L; between about 20 g/L and about 120 g/L; about 20 g/L and about 80 g/L; about 25 g/L and about 80 g/L; about 30 g/L and about 80 g/L; about 35 g/L and about 80 g/L; about 40 g/L and about 80 g/L; about 45 g/L and about 80 g/L; about 50 g/L and about 80 g/L; about 50 g/L and about 75 g/L; about 50 g/L and about 70 g/L; about 40 g/L and about 80 g/L.

Proteins of Interest

The methods and compositions of the present invention are useful for producing high levels of properly processed protein or polypeptide of interest in a cell expression system. The protein or polypeptide of interest can be of any species and of any size. However, in certain embodiments, the protein or polypeptide of interest is a therapeutically useful protein or polypeptide. In some embodiments, the protein can be a mammalian protein, for example a human protein, and can be, for example, a growth factor, a cytokine, a chemokine or a blood protein. The protein or polypeptide of interest can be processed in a similar manner to the native protein or polypeptide. In certain embodiments, the protein or polypeptide does not include a secretion signal in the coding sequence. In certain embodiments, the protein or polypeptide of interest is less than 100 kD, less than 50 kD, or less than 30 kD in size. In certain embodiments, the protein or polypeptide of interest is a polypeptide of at least about 5, 10, 15, 20, 30, 40, 50 or 100 amino acids.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank at the website //www.ncbi.nlm.nih.gov/Entrez. Additional information can also be obtained from GeneCards, an electronic encyclopedia integrating information about genes and their products and biomedical applications from the Weizmann Institute of Science Genome and Bioinformatics (bioinformatics.weizmann.ac.il/cards), nucleotide sequence information can be also obtained from the EMBL Nucleotide Sequence Database (www.ebi.ac.uk/embl/) or the DNA Databank or Japan (DDBJ, www.ddbi.nig.ac.ii/; additional sites for information on amino acid sequences include Georgetown's protein information resource website (www-nbrf.Georgetown.edu/pirl) and Swiss-Prot (au.expasy.org/sprot/sprot-top.html).

Examples of proteins that can be expressed in this invention include molecules such as, e.g., renin, a growth hormone, including human growth hormone; bovine growth hormone; growth hormone releasing factor; parathyroid hormone; thyroid stimulating hormone; lipoproteins; α-1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated polypeptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-β; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

In certain embodiments, the protein or polypeptide can be selected from IL-1, IL-1a, IL-1b, IL-2, IL-3, IL-4, IL-5, IL-6, IL-7, IL-8, IL-9, IL-10, IL-11, IL-12, IL-12elasti, IL-13, IL-15, IL-16, IL-18, IL-18BPa, IL-23, IL-24, VIP, erythropoietin, GM-CSF, G-CSF, M-CSF, platelet derived growth factor (PDGF), MSF, FLT-3 ligand, EGF, fibroblast growth factor (FGF; e.g., α-FGF (FGF-1), β-FGF (FGF-2), FGF-3, FGF-4, FGF-5, FGF-6, or FGF-7), insulin-like growth factors (e.g., IGF-1, IGF-2); tumor necrosis factors (e.g., TNF, Lymphotoxin), nerve growth factors (e.g., NGF), vascular endothelial growth factor (VEGF); interferons (e.g., IFN-α, IFN-β, IFN-γ); leukemia inhibitory factor (LIF); ciliary neurotrophic factor (CNTF); oncostatin M; stem cell factor (SCF); transforming growth factors (e.g., TGF-α, TGF-β11, TGF-β2, TGF-β3); TNF superfamily (e.g., LIGHT/TNFSF14, STALL-1/TNFSF13B (BLy5, BAFF, THANK), TNFalpha/TNFSF2 and TWEAK/TNFSF12); or chemokines (BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1/ABCD-1, MIP-1.quadrature., MIP-1.quadrature., MIP-2.quadrature./GRO.quadrature., MIP-3.quadrature./Exodus/LARC, MIP-3/Exodus-3/ELC, MIP-4/PARC/DC-CK1, PF-4, RANTES, SDF1, TARC, or TECK).

In one embodiment of the present invention, the protein of interest can be a multi-subunit protein or polypeptide. Multisubunit proteins that can be expressed include homomeric and heteromeric proteins. The multisubunit proteins may include two or more subunits, that may be the same or different. For example, the protein may be a homomeric protein comprising 2, 3, 4, 5, 6, 7, 8, 9, 10, 11, 12 or more subunits. The protein also may be a heteromeric protein including 2, 3, 4, 5, 6, 7, 8, 9, 10, 11, 12, or more subunits. Exemplary multisubunit proteins include: receptors including ion channel receptors; extracellular matrix proteins including chondroitin; collagen; immunomodulators including MHC proteins, full chain antibodies, and antibody fragments; enzymes including RNA polymerases, and DNA polymerases; and membrane proteins.

In another embodiment, the protein of interest can be a blood protein. The blood proteins expressed in this embodiment include but are not limited to carrier proteins, such as albumin, including human and bovine albumin, transferrin, recombinant transferrin half-molecules, haptoglobin, fibrinogen and other coagulation factors, complement components, immunoglobulins, enzyme inhibitors, precursors of substances such as angiotensin and bradykinin, insulin, endothelin, and globulin, including alpha, beta, and gamma-globulin, and other types of proteins, polypeptides, and fragments thereof found primarily in the blood of mammals. The amino acid sequences for numerous blood proteins have been reported (see, S. S. Baldwin (1993) Comp. Biochem Physiol. 106b:203-218), including the amino acid sequence for human serum albumin (Lawn, L. M., et al. (1981) Nucleic Acids Research, 9:6103-6114.) and human serum transferrin (Yang, F. et al. (1984) Proc. Natl. Acad. Sci. USA 81:2752-2756).

In another embodiment, the protein of interest can be a recombinant enzyme or co-factor. The enzymes and co-factors expressed in this embodiment include but are not limited to aldolases, amine oxidases, amino acid oxidases, aspartases, B12 dependent enzymes, carboxypeptidases, carboxyesterases, carboxylyases, chemotrypsin, CoA requiring enzymes, cyanohydrin synthetases, cystathione synthases, decarboxylases, dehydrogenases, alcohol dehydrogenases, dehydratases, diaphorases, dioxygenases, enoate reductases, epoxide hydrases, fumerases, galactose oxidases, glucose isomerases, glucose oxidases, glycosyltrasferases, methyltransferases, nitrile hydrases, nucleoside phosphorylases, oxidoreductases, oxynitilases, peptidases, glycosyltrasferases, peroxidases, enzymes fused to a therapeutically active polypeptide, tissue plasminogen activator; urokinase, reptilase, streptokinase; catalase, superoxide dismutase; Dnase, amino acid hydrolases (e.g., asparaginase, amidohydrolases); carboxypeptidases; proteases, trypsin, pepsin, chymotrypsin, papain, bromelain, collagenase; neuramimidase; lactase, maltase, sucrase, and arabinofuranosidases.

In another embodiment, the protein of interest can be a single chain, Fab fragment and/or full chain antibody or fragments or portions thereof. A single-chain antibody can include the antigen-binding regions of antibodies on a single stably-folded polypeptide chain. Fab fragments can be a piece of a particular antibody. The Fab fragment can contain the antigen binding site. The Fab fragment can contain 2 chains: a light chain and a heavy chain fragment. These fragments can be linked via a linker or a disulfide bond.

The coding sequence for the protein or polypeptide of interest can be a native coding sequence for the target polypeptide, if available, but will more preferably be a coding sequence that has been selected, improved, or optimized for use in the selected expression host cell: for example, by synthesizing the gene to reflect the codon use bias of the host cell. Genetic code selection and codon frequency enhancement may be performed according to any of the various methods known to one of ordinary skill in the art, e.g., oligonucleotide-directed mutagenesis. Useful on-line InterNet resources to assist in this process include, e.g.: (1) the Codon Usage Database of the Kazusa DNA Research Institute (2-6-7 Kazusa-kamatari, Kisarazu, Chiba 292-0818 Japan) and available at www.kazusa.orjp/codon; and (2) the Genetic Codes tables available from the NCBI Taxonomy database at www.ncbi.nln.nih.gov/-Taxonomy/Utils/wprintgc.cgi?mode=c. For example, *Pseudomonas* species are reported as utilizing Genetic Code Translation Table 11 of the NCBI Taxonomy site, and at the Kazusa site as exhibiting the codon usage frequency of the table shown at www.kazusa.or.jp/codon/cgibin.

The gene(s) that result will have been constructed within or will be inserted into one or more plasmids, which will then be transformed into the expression host cell. Nucleic acid or a polynucleotide said to be provided in an "expressible form" means nucleic acid or a polynucleotide that contains at least one gene that can be expressed by the selected expression host cell.

In certain embodiments, the protein of interest is, or is substantially homologous to, a native protein, such as a native mammalian or human protein. In these embodiments, the protein is not found in a concatameric form, but is linked only to a secretion signal and optionally a tag sequence for purification and/or recognition.

In other embodiments, the protein of interest is a protein that is active at a temperature from about 20 to about 42° C. In one embodiment, the protein is active at physiological temperatures and is inactivated when heated to high or extreme temperatures, such as temperatures over 65° C.

In other embodiments, the protein when produced also includes an additional targeting sequence, for example a sequence that targets the protein to the periplasm or to the extracellular medium. In one embodiment, the additional targeting sequence is operably linked to the carboxy-terminus of the protein. In another embodiment, the protein includes a secretion signal for an autotransporter, a two partner secretion system, a main terminal branch system or a fimbrial usher porin. See, for example, U.S. Patent Application Nos. 60/887,476 and 60/887,486, filed Jan. 31, 2007, herein incorporated by reference in their entireties).

The following examples are offered by way of illustration and not by way of limitation.

EXPERIMENTAL EXAMPLES

Mutant Selection

Plasmid pDOW2200 was transformed into *P. fluorescens* strain MB 101 and transformants were selected on LB+Kan$^{50}$ (50 µg/ml) plates. Transformant colonies from a single plate were scraped off and transferred into 2 ml of M9+Glu media. A 1×10$^{-6}$ dilution was made in M9+Glu and then 50 µl was plated onto LB+Kan$^{100}$, LB+Kan$^{150}$ and LB+Kan$^{200}$ plates. After 48 hours of growth at 30° C., five of the largest colonies from the Kan$^{150}$ and Kan$^{200}$ plates were each restreaked onto another plate of the same kanamycin concentration and then a single colony was inoculated into 3 ml of LB+Kan$^{150}$ or LB+Kan$^{200}$ respectively. Glycerol stocks of all the cultures were made and then from the same culture, Plasmid minipreps were made after O.D. normalizing the cultures (see below) of the five LB+Kan$^{200}$ transformants, including the pDOW2200 parent plasmid. Five microliters of uncut DNA from each O.D. normalized miniprep was fractionated on a 1.5% agarose gel for comparison of DNA yields. Clone K200-1 (LB+Kan$^{200}$ clone #1) was re-inoculated into 2 ml of LB+Kan$^{200}$ and grown to saturation overnight at 30° C. A 1×10$^{-2}$ dilution was made in M9+Glu and 50 µl plated onto a LB+Kan$^{500}$ plate. The plates were incubated at 30° C. for 48 hours. Again, 5 of the largest colonies were restreaked onto LB+Kan$^{500}$ plates and grown for 48 hours at 30° C. Single colonies were inoculated into 3 ml of LB+Kan$^{500}$ and incubated overnight at 30° C. and 300 rpm. As above, glycerol stocks of each of the 5 cultures were made and from the same culture, O.D. normalized minipreps were made. Five microliters of uncut plasmid DNA were fractionated on a 1.5% agarose gel for visual comparison of plasmid yield. Plasmid DNA from pDOW2200 and clone K500-4 was used to retransform MB101 cells. pDOW2200 transformants were selected on LB+Kan$^{50}$ while the K500-4 transformants were selected on LB+Kan$^{1,000}$ plates. The procedure of restreaking, making of glycerol stocks, O.D. normalized minipreps and plasmid yield visualization on agarose gels was repeated for kanamycin concentrations of 2,000, 5,000, 10,000 and 20,000 µg/ml. Plasmid DNA from each previous concentration was used to retransform MB101 and select for transformants at the next concentration. Only transformants from up to 5,000 µg/ml kan agar plates were culturable after being restreaked so this was the highest concentration of kanamycin used for collecting and studying the copy number mutants. Clone NK1000 ("new" K1000) was isolated when plasmid DNA from the original K1000-3 was retransformed into MB101 cells and selected on LB+Kan$^{1,000}$ plates.

Minipreps Made from O.D. Normalized Cultures

All clones were inoculated into 3 ml LB+Kan media for overnight growth at 30° C. and 300 rpm shaking. The amount of kanamycin used in each culture corresponded with the amount in the transformant plate upon which the clone was selected. After 16-18 hours of incubation, each culture density was read on the Eppendorf Biophotometer using 100 µl culture sample diluted into 900 µl of water and an optical density reading at A600. 1.2 ml of the lowest density culture was collected and the remaining culture volumes collected were normalized to an equivalent of what was collected for the lowest density culture (ie. lowest density culture O.D.=5.0, therefore 1.2 ml culture collected. Another culture has O.D.=6.0, therefore 1.0 ml of culture collected.). Once normalized culture volumes were collected, all samples processed for plasmid DNA using the Qiagen Spin Miniprep Kit (#27106). All samples eluted into 50 µl of TE (pH 8.0) buffer.

Glycerol Stocks

A portion of the cultures used for minipreps were also used to make glycerol stocks. 750 µl of each culture was mixed with 250 µl of 80% glycerol in a 1 ml Nunc cryotube and placed at −80° C. for storage.

Quantitative PCR (qPCR) for Estimating Plasmid Copy Number

To estimate plasmid copy number per cell, qPCR was used to quantify the DNA yields of plasmid preps made from O.D. normalized cultures. Plasmid DNA from the pDOW2200 parent as well as putative mutants K200, K500, K1000, NK1000, K2000 and K5000 was quantified using the MJ Opticon qPCR machine, the Invitrogen Platinum® SYBR® Green qPCR SuperMix UDG kit and corresponding protocol (#11733-038). The primers specific for pCN51 quantification are provided in Table 3 below.

TABLE 3 pCN51 primers

| NAME | PRIMER | SEQ ID NO: |
|---|---|---|
| pCNori1 | 5' GCATCGTGGTGTCACGCTCGTCGTT | 7 |
| pCNori2 | 5' TGCCGAGCTGTTGACCGCATATCC | 8 |

To reduce well-to-well variability, a master mix of reagents was prepared for immediate use and in enough quantity for use in all samples and blank wells. For fifty 20 µl reactions (1,000 µl Vf): 500 µl 2× SuperMix, 2.5 µl pCNori1 (0.25 µM Cf), 2.5 µl pCNori 2 (0.25 µM Cf), 245 µl sterile MilliQ water were mixed in a single tube. 15 µl of master mix was aliquoted per well. Five µl per well of prepared samples were added separately. All samples and reference DNA were prepared as dilutions of plasmid DNA in which 5 µl per well of sample would be added to the prepared and aliquoted master mix. Each sample was added to the plate in quadruplicate (4 wells per diluted sample). Sample dilutions ranged from no dilution or 1× (equivalent to 1 µl undiluted miniprep per well), 1/10, 1/100 and 1/1,000 fold. pCN51 reference DNA at a known amount of 0.04 ng/ml was added as a range of 5× (equivalent to 5 µl of undiluted DNA per well), 1×, 1/10 or 1/100 fold. All sample and reference data was entered into the Opticon data file and run with the following conditions: 50° C. for 2 min, 1×; 95° C. for 2 min, 1×; 95° C. for 15 sec., 64° C. for 30 sec., 72° C. for 30 sec., these three temperatures repeated 45 times; then, 72° C. for 5 min, 1×. Samples were quantitated automatically by the OpticonMONITOR v. 1.08 software. Averages of the 4 replicates were calculated and graphed on Excel.

Sequencing the Mutant Plasmids

Putative mutant plasmids K200, NK1000, K2000 and K5000 and the parent pDOW2200 plasmid were prepared using the Qiafilter Plasmid Maxi kit (Qiagen #12263) from 50 ml cultures grown in LB+Kan (concentration in µg/ml corresponds to the clone number) overnight at 30° C. and 300 rpm. Primers designed to sequence the entirety of pDOW2200 were utilized for this project and are listed in Table 4.

One-quarter reactions were used for all sequence samples using ABI BigDye V3.1 premix. Reactions consist of 3 µl 5× sequencing buffer, 2 µl premix, 1 µl 6.4 µM primer, 50 fmol of DNA template and $H_2O$ to adjust volume to 20 µl. Sequencing reactions were then purified using G-50 column (Millipore) and loaded into ABI3100. All sequence data was aligned using DNAStar Seqman software. The putative mutant plasmids were given pDOW numbers: K200=pDOW2425, NK1000=pDOW2426, K2000=pDOW2427 and K5000=pDOW2428.

Subcloning hGH into Mutant Plasmids for Expression Analysis

Plasmid pDOW1179 was used as the template for PCR amplification of the region spanning from the lacO (near the BamHI site) at the 5' end to the rrnB $T_1T_2$ terminator (near the PstI site) at the 3' end. Primers used for the amplification:

```
1179Bam:
AGGGAGCTCGCGCAAGCAGCGCCGTTGCG    (SEQ ID NO: 9)

1179Pst:
AGGGAGCTCGCTTCCAGATGTATGCTCTTC   (SEQ ID NO: 10)
```

Amplification reaction: 95° C. for 3 min, 1×; 95° C. for 30 sec., 55° C. for 60 sec., 72° C. for 2 min., these three temperatures repeated 30 times; then, 72° C. for 5 min., 1×; 4° C. hold. The PCR product was fractionated on a 1.5% agarose gel and purified using the Qiagen QiaexII kit (#20051). Vectors pDOW2200, NK1000 and K2000 were digested with SacI (New England Biolabs #R0156), phosphatased with BAP enzyme (Invitrogen #18011-015) and then purified over a Qiagen MinElute column (#28004). The purified PCR insert was ligated into each of the prepared vectors using T4 ligase (New England Biolabs #M0202S) in a 15 µl reaction. The ligation was incubated at 16° C. overnight, then ethanol precipitated and resuspended in 10 µl of sterile MilliQ water. 5 µl of each ligation was transformed into DC454 cells and selected on LB+Kan$^{50}$ plates. Six randomly chosen clones of each transformation were processed for miniprep DNA, restriction digested with HindIII and PstI (New England Biolabs #R0104 and R0140), and fractionated on a 1.5% agarose gel to confirm the presence and orientation of the promoter-hGH-terminator insert DNA. Parental plasmid pDOW2200 carrying the hGH-promoter-terminator insert was saved as pDOW2429. Plasmid NK1000 carrying the hGH-promoter-terminator insert was saved as pDOW2430. Plasmid K2000 carrying the hGH-promoter-terminator insert was saved as pDOW2431.

hGH 96 Well Expression Analysis

Three isolates of each clone, confirmed to have the promoter-hGH-terminator coding sequence by restriction analysis, were chosen to be grown in 96 well plates for analysis of protein expression. Single clones from freshly streaked plates were inoculated into 10 ml of LB+ura+Kan$^{50}$ and incubated in a 50 ml conical tube at 30° C., 300 rpm shaking overnight. The saturated overnight cultures were inoculated and grown according to the 96 well high throughput protocol (Retallack_et al., 2007, Biotech Letts 29(10): 1483-1491).

SDS-PAGE Analysis of pbp-hGH Expression

Samples for SDS-PAGE were taken at I0, I24 and I48. For each sample, the amounts of culture collected were equalized by O.D. A600 values [(O.D. 20/O.D. of well sample)×25 µl=# of µl to sample from well]. The normalized amount of culture was pipetted into a microfuge tube, pelleted for 3 minutes in the microfuge at top speed to pellet the cells and then the supernatant was pipetted off. The cell pellets were frozen at −80° C. for later processing.

Lysis of the cells was performed by using the EasyLyse kit and protocol (Epicentre #RP03750). Samples were then pelleted in the microfuge for 20 minutes at 4° C. The supernatant (soluble fraction) was pipetted into a new microfuge tube. The pellet (insoluble fraction) was then resuspended in an equal volume of 1×PBS. 25 µl of each fraction was mixed with an equal volume of 2× Laemmli Sample buffer (BioRad #161-0737). Samples were stored at −20° C. until ready to load on a gel. Prior to gel loading, samples were boiled for 5 minutes and then 15 µl of each sample was loaded onto a 12% Bis-Tris Criterion XT gel (BioRad #345-0119). Gels were stained using Bio-Safe Coomassie Stain (BioRad #161-0786). Imaging and densitometry were performed using the Alpha Innotech Fluor Chem 8800 machine and software.

RESULTS AND DISCUSSION

Figure 2:
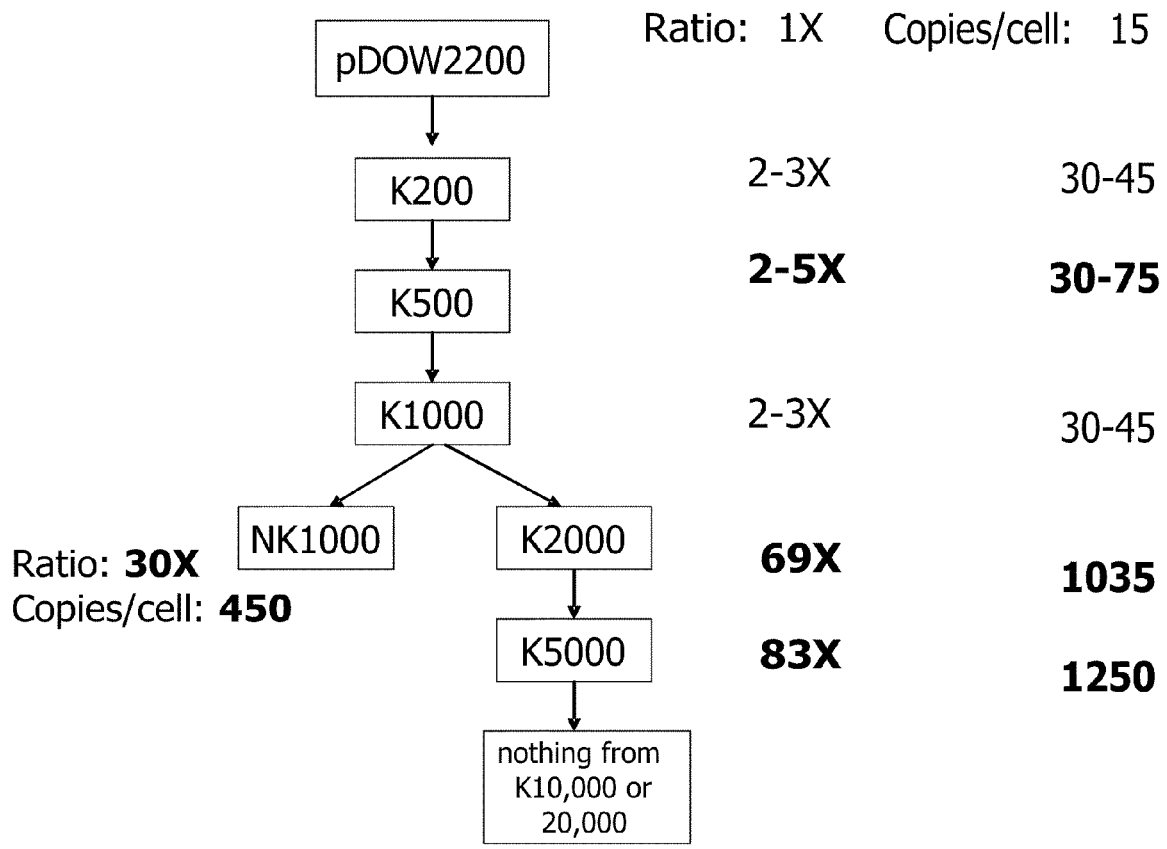
FIG. 2 is a workflow map of plasmid copy number mutants selected.

Selective pressure of increasing kanamycin concentrations was applied on a culture of *P. fluorescens* bearing recreated pCN51 plasmid, pDOW2200 (FIG. 1) as outlined in Materials and Methods. *P. fluorescens* strain MB101 was transformed with pDOW2200 and transformants were grown on LB plates containing increasing concentrations of kanamycin. This procedure was repeated several times until transformants could no longer be recovered (FIG. 2). The transformation process was repeated with each round of selection to eliminate any host chromosomal mutations which would cause the increased plasmid copy number. Clones of interest showed relatively higher yields of plasmid per cell as compared to the parent plasmid clone when standard minipreps of plasmid DNA were analyzed with agarose gels and by quantitative PCR (qPCR) (FIGS. 3a and 3b). qPCR showed putative mutant clones K200, NK1000, K2000 and K5000 to have plasmid yields approximately 3, 30, 69 and 83 times higher than the parent plasmid respectively. Knowing that the pCN51 vector is maintained at about 15 copies per cell, the increases in copy number equate to 45 for K200, 450 for NK1000, 1,035 for K2000 and 1,250 copies per cell for K5000 (FIG. 2). These copy number increases are readily apparent when equal volumes of plasmid maxiprep samples prepared from O.D. normalized cultures are fractionated and viewed on an agarose gel (FIG. 3a).

To verify that the increased plasmid copy numbers were a result of a mutation on the plasmid and not due to host mutations, the plasmids isolated from clones K200, NK1000, K2000 and K5000 were sequenced in their entirety. Interestingly, the K200 plasmid showed no mutations despite the fact that copy numbers were 2-5 times higher than the parent pDOW2200 plasmid. Plasmids isolated from clones K2000 and K5000 showed the same single base-pair mutation within the repA gene (base-pair 278 from the start of the ORF), a G to T conversion which results in the amino acid change from arginine to leucine at residue 93 (FIG. 4). It is surprising that this same mutation allowed the transformants of K5000 to survive at over twice the level of kanamycin used to select for the K2000 transformants despite the fact that these two plasmids are genotypically identical. These data taken together suggest that there is possibly a host cell factor(s) which can contribute to increasing plasmid copy number to a limited extent when challenged with increased antibiotic levels; there are numerous cellular factors which play a role in microbial survival responses for antibiotic resistance (Sheldon A T Jr., 2005). The plasmid NK1000 also has a single base-pair mutation in the repA gene (basepair 271 from the start of the ORF), a C to G conversion which results in the amino acid change from arginine to glycine at residue 91. The plasmid yields for NK1000 were 30× higher than the parental pDOW2200 plasmid. The mutant plasmids were given designations pDOW2425 for K200, pDOW2426 for NK1000, pDOW2427 for K2000 and pDOW2428 for K5000. Also worth noting is that both mutations in the repA gene which led to significantly higher copy numbers within the cell were very close to one another (only two amino acids apart) suggesting that this region is important for the binding of replication proteins and efficiency of plasmid replication as a whole.

When plasmids pDOW2425, pDOW2426, pDOW2427 and pDOW2428 were transformed into E. coli, strain DH5α, no difference in copy number among any of the plasmids was observed; they all showed high yields of plasmid (results not shown). This result is not surprising considering that the pBR322 replication region drives replication of these plasmids in E. coli and the repA gene, where the point mutations of these plasmids were identified, is specific to P. fluorescens.

Figure 6:
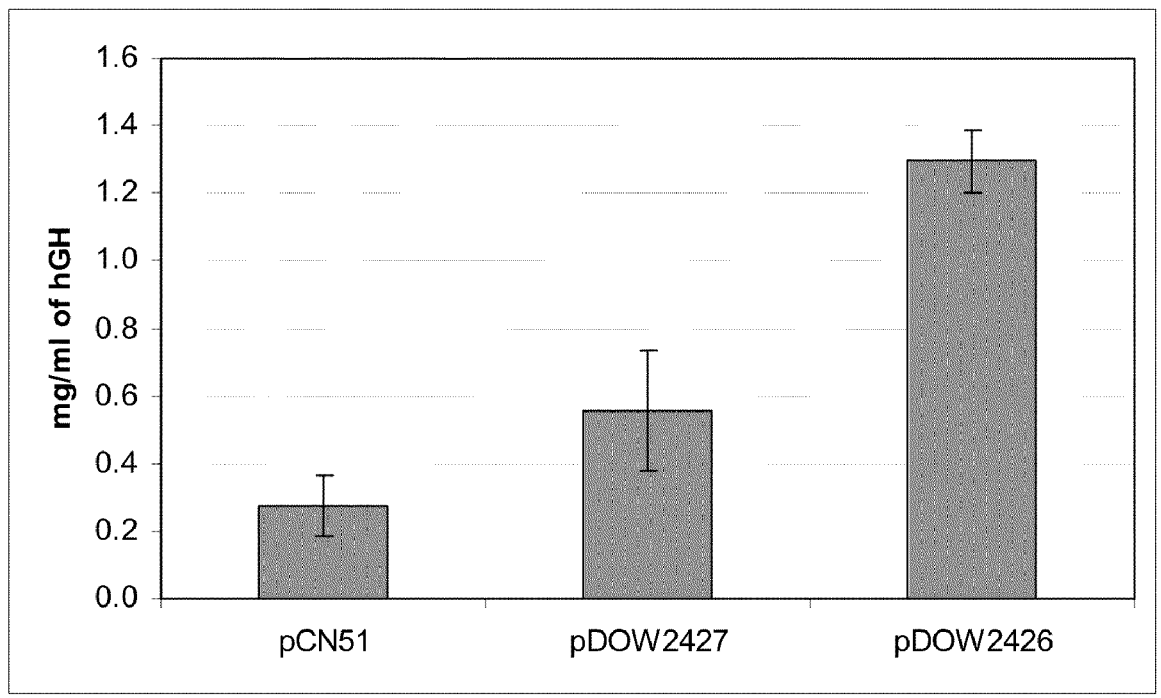
FIG. 6 shows the expression of recombinant human growth hormone (hGH) using pCN51 and its high copy number derivative plasmids.

To study the effect of the higher plasmid copy numbers on protein expression and accumulation, the coding region for cytoplasmically expressed hGH as well as accompanying tac promoter and rrnB $T_1T_2$ terminator sequences from plasmid pDOW1179 were subcloned into mutant plasmids pDOW2426 and pDOW2427. As a control, the hGH-promoter-terminator fragment was also subcloned into parent plasmid pDOW2200. The entire expression cassette from the tac promoter to the terminators was PCR amplified from the plasmid pDOW1179 with primers that incorporated SacI sites at each end of the fragment and then ligated into the pDOW2200, pDOW2426 and pDOW2427 vectors. These new plasmids were given designations pDOW2429 for pDOW2200+hGH, pDOW2430 for pDOW2426+hGH and pDOW2431 for pDOW2427+hGH. Ligations were transformed into P. fluorescens strain DC454 and transformants were selected on standard LB+Kan$^{50}$ plates with uracil supplemented. Fragment insertion and orientation were determined by restriction digest analysis of miniprep DNA of the transformants. Transformants chosen for expression analysis were given designations DC671 for pDOW2429 in DC454, DC672 for pDOW2431 in DC454 and DC673 for pDOW2430 in DC454. Growth, expression and analysis of the clones were carried out in a 96 well plate using HTP conditions with a constant Kan$^{50}$ selection (Retallack_et al., 2007, Biotech Letts 29(10): 1483-1491). Kan$^{50}$ was used for all three recombinant strains to demonstrate that the mutant plasmids could maintain higher copy number levels and higher expression levels than the parental control under standard kanamycin concentrations. Soluble and insoluble fractions were fractionated on 12% Bis-Tris Criterion XT gels next to hGH protein standard. Gels were imaged and scanning densitometry was performed using the Alpha Innotech Fluor Chem 8800 machine and software. Analysis of the plasmid copy number from each culture on agarose gels before and after the expression experiment showed varying results. Yields of plasmid from the seed cultures showed that DC672 and DC673 yielded significantly higher levels of plasmid than DC671. Yields of plasmid at 48 hr post-induction however, showed that plasmid yield from DC672 and DC673 decreased during the course of the experiment with DC672 showing the highest plasmid yield. Analysis of protein yields on SDS-PAGE gels showed the yield of soluble hGH was similar in all of the strains—approximately 0.2-0.4 mg/ml. The yield of insoluble hGH varied among the different recombinant strains. DC671 had no visible insoluble hGH, DC672 yielded low amounts of insoluble hGH (approximately 0.15 mg/ml) and DC673 yielded insoluble hGH 2-4× higher than the soluble fractions (approximately 0.8-1.2 mg/ml). The insoluble data is supported by viewing the cells under the microscope. DC671 had no visible inclusion bodies, DC672 had one small inclusion body per cell and DC673 showed 1-2 large inclusion bodies per cell. Total hGH yield among the three strains is shown graphically in FIG. 6. The entire expression experiment was repeated and showed similar results. Table 5 shows the plasmids and Table 6 shows the strains used in this study. Except for plasmid yields seen at the end of the expression experiments, these results contradict what would be expected from the hGH expression experiments; that the higher the starting copy number of the plasmid, the higher the yield of expressed protein. It has been observed that plasmid copy numbers that are too high within bacterial expression systems can actually lead to a decrease in protein production and yield. One possible explanation is that the cell is spending too much energy and resources in plasmid replication rather than protein production (Bagdasarian M. and Timmis K N, 1981). That could very well explain the results seen in our expression experiments between DC672 and DC673. This is also why the preferred pET expression vectors in E. coli are lower copy number than the high copy number pUC9 based cloning vectors.

REFERENCES

Bagdasarian M and Timmis K N. 1981. Host:vector systems for gene cloning in *Pseudomonas*. Curr. Topics Microbiol. Immunol. 96:47-67.

Cabello F, Timmis K. and Cohen S N. 1976. Replication control in a composite plasmid constructed by in vitro linkage of two distinct replicons. Nature (London) 259: 285-290.

Drake J W, Charlesworth B, Charlesworth D and Crow J F. 1998. Rates of Spontaneous Mutation. Genetics 148: 1667-1686.

Maestro B, Sanz J M, Diaz-Orejas R, Fernandez-Tresguerres E. 2003. Modulation of pPS10 host range by plasmid-encoded RepA initiator protein. J. Bacteriol. 185(4): 1367-1375.

Nieto C., Fernandez-Tresguerres E., Sanchez N., Vicente M., Diaz R. 1990. Cloning vectors, derived from a naturally occurring plasmid of *Pseudomonas savastanoi*, specifically tailored for genetic manipulations in *Pseudomonas*. Gene 87: 145-149.

Scorer C A, Clare J J, McCombie W R, Romanos M A, Sreekrishna K. 1994. Rapid selection using G418 of high copy number transformants of *Pichia pastoris* for high-level foreign gene expression. Biotechnology (N Y). 12(2): 181-4.

Sheldon A T Jr. 2005. Antibiotic resistance: a survival strategy. Clin Lab Sci. 18(3): 170-180.

TABLE 4

Primers used for sequencing putative mutant plasmids K200, NK1000, K2000 and K5000.

| Primer Name | Primer Sequence | SEQ ID NO: |
|---|---|---|
| C1 | TGTGGTTAGGTCCAGTTGGGG | 11 |
| C4 | AATGATTCGTCGGCCCTGTCGG | 12 |
| C5 | GACTGCGTGACTTTGTTCTCGAC | 13 |
| C6 | TCGCGCGTTTCGGTGATGAC | 14 |
| C7 | TGTTCCGACCCTGCCGCTTA | 15 |
| C8 | AGTAAACTTGGTCTGACAGT | 16 |
| C9 | AAAAATTCGGCAGGGTTTCG | 17 |
| C10 | TTGCATATCGCCGTCATCGG | 18 |
| C11 | GCTGACGGAATTTATGCCTCTTC | 19 |
| C12 | TTGGTTAATTGGTTGTAACACTGGC | 20 |
| C13 | TGAGGGAGCCACGGTTGATG | 21 |
| C14 | CGATCGCTGTTAAAAGGACAATTAC | 22 |
| C15 | CGTTCCGTGGCAAAGCAAAA | 23 |
| C16 | TATCTGGCAGAGAACCCGCAGG | 24 |
| C17 | GCTGGCTGGTTTATTGCTGATAA | 25 |
| C18 | CGATAAGTCGTGTCTTACCGGG | 26 |
| C19 | TCTGATGCCGCATAGTTAAGCC | 27 |
| C20 | TTAAAGGGGACAGATTCAGGGTTT | 28 |
| C21 | GCTGTCCGCCTTTACGAGCTT | 29 |
| C22 | TTGACACGGTACCGGTCGAC | 30 |
| C24 | GCCATTCGATGGTGTCAACGTAA | 31 |
| p2200-A | GGAAGGGTTGTTTCTGTAGA | 32 |
| p2200-B | GAAGGCTTTGAGAGAGGAGG | 33 |

TABLE 4-continued

Primers used for sequencing putative mutant plasmids K200, NK1000, K2000 and K5000.

| Primer Name | Primer Sequence | SEQ ID NO: |
|---|---|---|
| p2200-C | ATGGTCGAGAACAAAGTCAC | 34 |
| p2200-D | ATCTGATCCTTCAACTCAGC | 35 |
| p2200-E | GTCCACCTACAACAAAGCTC | 36 |

TABLE 5

Strains

| Strain | Description |
|---|---|
| | MB101/pDOW2200 |
| K200 | MB101/pDOW2200 mutant isolated with 200 ug/mL kanamycin sulfate |
| NK1000 | MB101/pDOW2200 mutant isolated with 1000 ug/mL kanamycin sulfate |
| K2000 | MB101/pDOW2200 mutant isolated with 2000 ug/mL kanamycin sulfate |
| K5000 | MB101/pDOW2200 mutant isolated with 5000 ug/mL kanamycin sulfate |
| DC671 | DC454/pDOW2429 |
| DC672 | DC454/pDOW2431 |
| DC673 | DC454/pDOW2430 |

TABLE 6

Plasmids

| Plasmid | Description |
|---|---|
| pDOW2200 | Parental pCN51 plasmid |
| pDOW2425 | pDOW2200 mutant in strain K200 |
| pDOW2426 | pDOW2200 mutant in strain NK1000 |
| pDOW2427 | pDOW2200 mutant in strain K2000 |
| pDOW2428 | pDOW2200 mutant in strain K5000 |
| pDOW2429 | pDOW2200 with the hGH expression cassette |
| pDOW2430 | pDOW2426 with the hGH expression cassette |
| pDOW2431 | pDOW2427 with the hGH expression cassette |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A plasmid having an improved copy number compared to a control plasmid, wherein said improved copy number plasmid has a mutation in a replication control region of said improved copy number plasmid relative to the replication control region of said control plasmid, and wherein said control plasmid comprises the replication control region sequence set forth in SEQ ID NO: 1 or a nucleotide sequence encoding the amino acid sequence set forth in SEQ ID NO:2, wherein the mutation in said improved copy number plasmid results in a change in the amino acid corresponding to:
   a. residue 91 of SEQ ID NO:2, wherein residue 91 is changed to a glycine or a conservative substitution of glycine, and wherein the copy number of the improved copy number plasmid is about 15-fold to about 35-fold higher than that of the control plasmid, or;
   b. residue 93 of SEQ ID NO:2, wherein residue 93 is changed to a leucine or a conservative substitution of leucine, and wherein the copy number of the improved copy number plasmid is about 15-fold to about 83-fold higher than that of the control plasmid.

2. The improved copy number plasmid of claim 1, wherein said improved copy number plasmid comprises a nucleotide sequence selected from the group consisting of:
   a) the nucleotide sequence set forth in SEQ ID NO:3 or 5; and,
   b) a nucleotide sequence encoding the amino acid sequence set forth in SEQ ID NO:4 or 6.

3. The improved copy number plasmid of claim 1(a), wherein the copy number of said improved copy number plasmid is about 20-fold to about 35-fold higher than that of said control plasmid.

4. The improved copy number plasmid of claim 3, wherein the copy number of said improved copy number plasmid is about 25-fold to about 35-fold higher than that of said control plasmid.

5. The improved copy number plasmid of claim 4, wherein the copy number of said improved copy number plasmid is about 30-fold to about 35-fold higher than that of said control plasmid.

6. The improved copy number plasmid of claim 1, wherein said improved copy number plasmid and said control plasmid further comprise a selectable marker gene.

7. The improved copy number plasmid of claim 6, wherein said selectable marker gene confers resistance to kanamycin or gentamycin.

8. The improved copy number plasmid of claim 1, wherein said improved copy number plasmid further comprises a nucleotide sequence encoding a protein of interest.

9. The improved copy number plasmid of claim 1, wherein said improved copy number plasmid is capable of replication in a *Pseudomonas* host cell.

10. The improved copy number plasmid of claim 9, wherein said *Pseudomonas* host cell is *Pseudomonas fluorescens*.

11. A host cell comprising the improved copy number plasmid of claim 1, wherein said host cell is a *Pseudomonas* host cell.

12. The host cell of claim 11, wherein said *Pseudomonas* host cell is *Pseudomonas fluorescens*.

13. A method for the recombinant production of a protein of interest comprising introducing the improved copy number plasmid of claim 8 into a *Pseudomonas* host cell and maintaining said *Pseudomonas* host cell under conditions sufficient for the expression of the nucleotide sequence encoding the protein of interest.

14. The method of claim 13, wherein the amount of recoverable protein produced by said *Pseudomonas* host cell is increased relative to the amount of recoverable protein of said control plasmid, wherein said control plasmid comprises said nucleotide sequence encoding the protein of interest.

15. The improved copy number plasmid of claim 1(a), wherein the copy number of said improved copy number plasmid is about 30-fold higher than that of said control plasmid.

16. The improved copy number plasmid of claim 1(b), wherein the copy number of said improved copy number plasmid is about 25-fold to about 83-fold higher than that of said control plasmid.

17. The improved copy number plasmid of claim 16, wherein the copy number of said improved copy number plasmid is about 35-fold to about 83-fold higher than that of said control plasmid.

18. The improved copy number plasmid of claim 17, wherein the copy number of said improved copy number plasmid is about 50-fold to about 83-fold higher than that of said control plasmid.

19. The improved copy number plasmid of claim 18, wherein the copy number of said improved copy number plasmid is about 65-fold to about 83-fold higher than that of said control plasmid.

20. The improved copy number plasmid of claim 19, wherein the copy number of said improved copy number plasmid is about 70-fold to about 83-fold higher than that of said control plasmid.

21. The improved copy number plasmid of claim 19, wherein the copy number of said improved copy number plasmid is about 69-fold to about 83-fold higher than that of said control plasmid.

22. The improved copy number plasmid of claim 1(b), wherein the copy number of said improved copy number plasmid is about 69-fold higher than that of said control plasmid.

23. The improved copy number plasmid of claim 1(b), wherein the copy number of said improved copy number plasmid is about 83-fold higher than that of said control plasmid.

* * * * *

SEQUENCE LISTING

<160> NUMBER OF SEQ ID NOS: 36

<210> SEQ ID NO 1
<211> LENGTH: 690
<212> TYPE: DNA
<213> ORGANISM: Pseudomonas fluorescens
<220> FEATURE:

<220> NAME/KEY: CDS
<222> LOCATION: (1)...(690)

<400> SEQUENCE: 1

```
atg gtc gag aac aaa gtc acg cag tcc aat aaa ctc atc gaa tcg tca       48
Met Val Glu Asn Lys Val Thr Gln Ser Asn Lys Leu Ile Glu Ser Ser
 1               5                  10                  15 cat acg ttg aca ctc aat gag aaa cgc cta gtg cta tgc gct gcg tct       96
His Thr Leu Thr Leu Asn Glu Lys Arg Leu Val Leu Cys Ala Ala Ser
             20                  25                  30 ttg atc gat tca cgt aag cca ctc cct aaa gat ggt tac ttg acc atc      144
Leu Ile Asp Ser Arg Lys Pro Leu Pro Lys Asp Gly Tyr Leu Thr Ile
         35                  40                  45 cga gct gac acc ttc gct gag gtg ttt gga att gat gtc aaa cac gcc      192
Arg Ala Asp Thr Phe Ala Glu Val Phe Gly Ile Asp Val Lys His Ala
     50                  55                  60 tat gcg gca tta gat gac gct gcc aca aag ttg ttt aac cga gat att      240
Tyr Ala Ala Leu Asp Asp Ala Ala Thr Lys Leu Phe Asn Arg Asp Ile
 65                  70                  75                  80 cgc agg tac gtc aaa ggc aaa gtc gtt gaa cgc atg cgc tgg gtt ttt      288
Arg Arg Tyr Val Lys Gly Lys Val Val Glu Arg Met Arg Trp Val Phe
                 85                  90                  95 cac gtc aag tac agg gaa ggc caa ggc tgc gtc gag cta gga ttt tct      336
His Val Lys Tyr Arg Glu Gly Gln Gly Cys Val Glu Leu Gly Phe Ser
            100                 105                 110 cct acg ata atc ccg cat cta acc atg ctg cac aaa gag ttc acc agc      384
Pro Thr Ile Ile Pro His Leu Thr Met Leu His Lys Glu Phe Thr Ser
        115                 120                 125 tat cag ctc aag caa atc ggt agc ctg tcc agc ttc tac gct gtc cgc      432
Tyr Gln Leu Lys Gln Ile Gly Ser Leu Ser Ser Phe Tyr Ala Val Arg
    130                 135                 140 ctt tac gag ctt atg agc caa ttt atc aag ctc aaa cag cgg gaa tgc      480
Leu Tyr Glu Leu Met Ser Gln Phe Ile Lys Leu Lys Gln Arg Glu Cys
145                 150                 155                 160 aca ctc gcc caa ctg cgg gaa atg ttc gac ctt ggt gac aag tac caa      528
Thr Leu Ala Gln Leu Arg Glu Met Phe Asp Leu Gly Asp Lys Tyr Gln
                165                 170                 175 gac gtt aag gac atg cgt aag cgt gtg cta tat ccc gct tta gag gaa      576
Asp Val Lys Asp Met Arg Lys Arg Val Leu Tyr Pro Ala Leu Glu Glu
            180                 185                 190 gtg aac aag aac acc gat ttg aca gtg gca gtg gag cct cgc cga cag      624
Val Asn Lys Asn Thr Asp Leu Thr Val Ala Val Glu Pro Arg Arg Gln
        195                 200                 205 ggc cga cga atc att ggg ttc tca ttc acg atc gct aaa aac gat caa      672
Gly Arg Arg Ile Ile Gly Phe Ser Phe Thr Ile Ala Lys Asn Asp Gln
    210                 215                 220 ctg gca ctg agt ctc gag                                              690
Leu Ala Leu Ser Leu Glu
225                 230
```

<210> SEQ ID NO 2
<211> LENGTH: 230
<212> TYPE: PRT
<213> ORGANISM: Pseudomonas fluorescens

<400> SEQUENCE: 2

```
Met Val Glu Asn Lys Val Thr Gln Ser Asn Lys Leu Ile Glu Ser Ser
 1               5                  10                  15

His Thr Leu Thr Leu Asn Glu Lys Arg Leu Val Leu Cys Ala Ala Ser
             20                  25                  30

Leu Ile Asp Ser Arg Lys Pro Leu Pro Lys Asp Gly Tyr Leu Thr Ile
```

```
                    35                    40                    45
Arg Ala Asp Thr Phe Ala Glu Val Phe Gly Ile Asp Val Lys His Ala
 50                    55                    60

Tyr Ala Ala Leu Asp Asp Ala Ala Thr Lys Leu Phe Asn Arg Asp Ile
65                     70                    75                    80

Arg Arg Tyr Val Lys Gly Lys Val Val Glu Gly Met Arg Trp Val Phe
                    85                    90                    95

His Val Lys Tyr Arg Glu Gly Gln Gly Cys Val Glu Leu Gly Phe Ser
                100                   105                   110

Pro Thr Ile Ile Pro His Leu Thr Met Leu His Lys Glu Phe Thr Ser
            115                   120                   125

Tyr Gln Leu Lys Gln Ile Gly Ser Leu Ser Ser Phe Tyr Ala Val Arg
        130                   135                   140

Leu Tyr Glu Leu Met Ser Gln Phe Ile Lys Leu Lys Gln Arg Glu Cys
145                   150                   155                   160

Thr Leu Ala Gln Leu Arg Glu Met Phe Asp Leu Gly Asp Lys Tyr Gln
                165                   170                   175

Asp Val Lys Asp Met Arg Lys Arg Val Leu Tyr Pro Ala Leu Glu Glu
                180                   185                   190

Val Asn Lys Asn Thr Asp Leu Thr Val Ala Val Glu Pro Arg Arg Gln
            195                   200                   205

Gly Arg Arg Ile Ile Gly Phe Ser Phe Thr Ile Ala Lys Asn Asp Gln
        210                   215                   220

Leu Ala Leu Ser Leu Glu
225                 230

<210> SEQ ID NO 3
<211> LENGTH: 690
<212> TYPE: DNA
<213> ORGANISM: Artificial Sequence
<220> FEATURE:
<223> OTHER INFORMATION: repA mutant identified from plasmid pDOW2426
      (NK1000)
<221> NAME/KEY: CDS
<222> LOCATION: (1)...(690)

<400> SEQUENCE: 3 atg gtc gag aac aaa gtc acg cag tcc aat aaa ctc atc gaa tcg tca        48
Met Val Glu Asn Lys Val Thr Gln Ser Asn Lys Leu Ile Glu Ser Ser
1               5                   10                  15 cat acg ttg aca ctc aat gag aaa cgc cta gtg cta tgc gct gcg tct        96
His Thr Leu Thr Leu Asn Glu Lys Arg Leu Val Leu Cys Ala Ala Ser
            20                  25                  30 ttg atc gat tca cgt aag cca ctc cct aaa gat ggt tac ttg acc atc       144
Leu Ile Asp Ser Arg Lys Pro Leu Pro Lys Asp Gly Tyr Leu Thr Ile
        35                  40                  45 cga gct gac acc ttc gct gag gtg ttt gga att gat gtc aaa cac gcc       192
Arg Ala Asp Thr Phe Ala Glu Val Phe Gly Ile Asp Val Lys His Ala
 50                  55                  60 tat gcg gca tta gat gac gct gcc aca aag ttg ttt aac cga gat att       240
Tyr Ala Ala Leu Asp Asp Ala Ala Thr Lys Leu Phe Asn Arg Asp Ile
65                   70                  75                  80 cgc agg tac gtc aaa ggc aaa gtc gtt gaa ggc atg cgc tgg gtt ttt       288
Arg Arg Tyr Val Lys Gly Lys Val Val Glu Gly Met Arg Trp Val Phe
                 85                  90                  95 cac gtc aag tac agg gaa ggc caa ggc tgc gtc gag cta gga ttt tct       336
His Val Lys Tyr Arg Glu Gly Gln Gly Cys Val Glu Leu Gly Phe Ser
             100                 105                 110 cct acg ata atc ccg cat cta acc atg ctg cac aaa gag ttc acc agc       384
```

```
Pro Thr Ile Ile Pro His Leu Thr Met Leu His Lys Glu Phe Thr Ser
            115                 120                 125 tat cag ctc aag caa atc ggt agc ctg tcc agc ttc tac gct gtc cgc      432
Tyr Gln Leu Lys Gln Ile Gly Ser Leu Ser Ser Phe Tyr Ala Val Arg
        130                 135                 140 ctt tac gag ctt atg agc caa ttt atc aag ctc aaa cag cgg gaa tgc      480
Leu Tyr Glu Leu Met Ser Gln Phe Ile Lys Leu Lys Gln Arg Glu Cys
145                 150                 155                 160 aca ctc gcc caa ctg cgg gaa atg ttc gac ctt ggt gac aag tac caa      528
Thr Leu Ala Gln Leu Arg Glu Met Phe Asp Leu Gly Asp Lys Tyr Gln
                165                 170                 175 gac gtt aag gac atg cgt aag cgt gtg cta tat ccc gct tta gag gaa      576
Asp Val Lys Asp Met Arg Lys Arg Val Leu Tyr Pro Ala Leu Glu Glu
            180                 185                 190 gtg aac aag aac acc gat ttg aca gtg gca gtg gag cct cgc cga cag      624
Val Asn Lys Asn Thr Asp Leu Thr Val Ala Val Glu Pro Arg Arg Gln
        195                 200                 205 ggc cga cga atc att ggg ttc tca ttc acg atc gct aaa aac gat caa      672
Gly Arg Arg Ile Ile Gly Phe Ser Phe Thr Ile Ala Lys Asn Asp Gln
210                 215                 220 ctg gca ctg agt ctc gag                                              690
Leu Ala Leu Ser Leu Glu
225                 230

<210> SEQ ID NO 4
<211> LENGTH: 230
<212> TYPE: PRT
<213> ORGANISM: Artificial Sequence
<220> FEATURE:
<223> OTHER INFORMATION: RepA mutant identified from plasmid pDOW2426
      (NK1000)

<400> SEQUENCE: 4

Met Val Glu Asn Lys Val Thr Gln Ser Asn Lys Leu Ile Glu Ser Ser
1               5                   10                  15

His Thr Leu Thr Leu Asn Glu Lys Arg Leu Val Leu Cys Ala Ala Ser
            20                  25                  30

Leu Ile Asp Ser Arg Lys Pro Leu Pro Lys Asp Gly Tyr Leu Thr Ile
        35                  40                  45

Arg Ala Asp Thr Phe Ala Glu Val Phe Gly Ile Asp Val Lys His Ala
    50                  55                  60

Tyr Ala Ala Leu Asp Asp Ala Ala Thr Lys Leu Phe Asn Arg Asp Ile
65                  70                  75                  80

Arg Arg Tyr Val Lys Gly Lys Val Val Glu Gly Met Arg Trp Val Phe
                85                  90                  95

His Val Lys Tyr Arg Glu Gly Gln Gly Cys Val Glu Leu Gly Phe Ser
            100                 105                 110

Pro Thr Ile Ile Pro His Leu Thr Met Leu His Lys Glu Phe Thr Ser
        115                 120                 125

Tyr Gln Leu Lys Gln Ile Gly Ser Leu Ser Ser Phe Tyr Ala Val Arg
    130                 135                 140

Leu Tyr Glu Leu Met Ser Gln Phe Ile Lys Leu Lys Gln Arg Glu Cys
145                 150                 155                 160

Thr Leu Ala Gln Leu Arg Glu Met Phe Asp Leu Gly Asp Lys Tyr Gln
                165                 170                 175

Asp Val Lys Asp Met Arg Lys Arg Val Leu Tyr Pro Ala Leu Glu Glu
            180                 185                 190

Val Asn Lys Asn Thr Asp Leu Thr Val Ala Val Glu Pro Arg Arg Gln
        195                 200                 205
```

```
Gly Arg Arg Ile Ile Gly Phe Ser Phe Thr Ile Ala Lys Asn Asp Gln
    210                 215                 220

Leu Ala Leu Ser Leu Glu
225                 230

<210> SEQ ID NO 5
<211> LENGTH: 690
<212> TYPE: DNA
<213> ORGANISM: Artificial Sequence
<220> FEATURE:
<223> OTHER INFORMATION: repA mutant identified from plasmid pDOW2427
      (K2000)
<221> NAME/KEY: CDS
<222> LOCATION: (1)...(690)

<400> SEQUENCE: 5 atg gtc gag aac aaa gtc acg cag tcc aat aaa ctc atc gaa tcg tca      48
Met Val Glu Asn Lys Val Thr Gln Ser Asn Lys Leu Ile Glu Ser Ser
1               5                   10                  15 cat acg ttg aca ctc aat gag aaa cgc cta gtg cta tgc gct gcg tct      96
His Thr Leu Thr Leu Asn Glu Lys Arg Leu Val Leu Cys Ala Ala Ser
            20                  25                  30 ttg atc gat tca cgt aag cca ctc cct aaa gat ggt tac ttg acc atc     144
Leu Ile Asp Ser Arg Lys Pro Leu Pro Lys Asp Gly Tyr Leu Thr Ile
        35                  40                  45 cga gct gac acc ttc gct gag gtg ttt gga att gat gtc aaa cac gcc     192
Arg Ala Asp Thr Phe Ala Glu Val Phe Gly Ile Asp Val Lys His Ala
    50                  55                  60 tat gcg gca tta gat gac gct gcc aca aag ttg ttt aac cga gat att     240
Tyr Ala Ala Leu Asp Asp Ala Ala Thr Lys Leu Phe Asn Arg Asp Ile
65                  70                  75                  80 cgc agg tac gtc aaa ggc aaa gtc gtt gaa cgc atg ctc tgg gtt ttt     288
Arg Arg Tyr Val Lys Gly Lys Val Val Glu Arg Met Leu Trp Val Phe
                85                  90                  95 cac gtc aag tac agg gaa ggc caa ggc tgc gtc gag cta gga ttt tct     336
His Val Lys Tyr Arg Glu Gly Gln Gly Cys Val Glu Leu Gly Phe Ser
            100                 105                 110 cct acg ata atc ccg cat cta acc atg ctg cac aaa gag ttc acc agc     384
Pro Thr Ile Ile Pro His Leu Thr Met Leu His Lys Glu Phe Thr Ser
        115                 120                 125 tat cag ctc aag caa atc ggt agc ctg tcc agc ttc tac gct gtc cgc     432
Tyr Gln Leu Lys Gln Ile Gly Ser Leu Ser Ser Phe Tyr Ala Val Arg
    130                 135                 140 ctt tac gag ctt atg agc caa ttt atc aag ctc aaa cag cgg gaa tgc     480
Leu Tyr Glu Leu Met Ser Gln Phe Ile Lys Leu Lys Gln Arg Glu Cys
145                 150                 155                 160 aca ctc gcc caa ctg cgg gaa atg ttc gac ctt ggt gac aag tac caa     528
Thr Leu Ala Gln Leu Arg Glu Met Phe Asp Leu Gly Asp Lys Tyr Gln
                165                 170                 175 gac gtt aag gac atg cgt aag cgt gtg cta tat ccc gct tta gag gaa     576
Asp Val Lys Asp Met Arg Lys Arg Val Leu Tyr Pro Ala Leu Glu Glu
            180                 185                 190 gtg aac aag aac acc gat ttg aca gtg gca gtg gag cct cgc cga cag     624
Val Asn Lys Asn Thr Asp Leu Thr Val Ala Val Glu Pro Arg Arg Gln
        195                 200                 205 ggc cga cga atc att ggg ttc tca ttc acg atc gct aaa aac gat caa     672
Gly Arg Arg Ile Ile Gly Phe Ser Phe Thr Ile Ala Lys Asn Asp Gln
    210                 215                 220 ctg gca ctg agt ctc gag                                             690
Leu Ala Leu Ser Leu Glu
225                 230
```

<210> SEQ ID NO 6
<211> LENGTH: 230
<212> TYPE: PRT
<213> ORGANISM: Artificial Sequence
<220> FEATURE:
<223> OTHER INFORMATION: RepA mutant identified from plasmid pDOW2427 (K2000)

<400> SEQUENCE: 6

Met Val Glu Asn Lys Val Thr Gln Ser Asn Lys Leu Ile Glu Ser Ser
 1               5                  10                  15

His Thr Leu Thr Leu Asn Glu Lys Arg Leu Val Leu Cys Ala Ala Ser
             20                  25                  30

Leu Ile Asp Ser Arg Lys Pro Leu Pro Lys Asp Gly Tyr Leu Thr Ile
         35                  40                  45

Arg Ala Asp Thr Phe Ala Glu Val Phe Gly Ile Asp Val Lys His Ala
     50                  55                  60

Tyr Ala Ala Leu Asp Asp Ala Ala Thr Lys Leu Phe Asn Arg Asp Ile
65                  70                  75                  80

Arg Arg Tyr Val Lys Gly Lys Val Val Glu Arg Met Leu Trp Val Phe
                 85                  90                  95

His Val Lys Tyr Arg Glu Gly Gln Gly Cys Val Glu Leu Gly Phe Ser
            100                 105                 110

Pro Thr Ile Ile Pro His Leu Thr Met Leu His Lys Glu Phe Thr Ser
        115                 120                 125

Tyr Gln Leu Lys Gln Ile Gly Ser Leu Ser Ser Phe Tyr Ala Val Arg
    130                 135                 140

Leu Tyr Glu Leu Met Ser Gln Phe Ile Lys Leu Lys Gln Arg Glu Cys
145                 150                 155                 160

Thr Leu Ala Gln Leu Arg Glu Met Phe Asp Leu Gly Asp Lys Tyr Gln
                165                 170                 175

Asp Val Lys Asp Met Arg Lys Arg Val Leu Tyr Pro Ala Leu Glu Glu
            180                 185                 190

Val Asn Lys Asn Thr Asp Leu Thr Val Ala Val Glu Pro Arg Arg Gln
        195                 200                 205

Gly Arg Arg Ile Ile Gly Phe Ser Phe Thr Ile Ala Lys Asn Asp Gln
    210                 215                 220

Leu Ala Leu Ser Leu Glu
225                 230

<210> SEQ ID NO 7
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 7
gcatcgtggt gtcacgctcg tcgtt                                          25

<210> SEQ ID NO 8
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 8
tggccgagct gttgaccgca tatcc                                          25

<210> SEQ ID NO 9
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 9
agggagctcg cgcaagcagc gccgttgcg                                29

<210> SEQ ID NO 10
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 10
agggagctcg cttccagatg tatgctcttc                               30

<210> SEQ ID NO 11
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 11
tgtggttagg tccagttggg g                                        21

<210> SEQ ID NO 12
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 12
aatgattcgt cggccctgtc gg                                       22

<210> SEQ ID NO 13
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 13
gactgcgtga ctttgttctc gac                                      23

<210> SEQ ID NO 14
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 14
tcgcgcgttt cggtgatgac                                          20

<210> SEQ ID NO 15
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 15
tgttccgacc ctgccgctta                                        20

<210> SEQ ID NO 16
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 16
agtaaacttg gtctgacagt                                        20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 17
aaaaattcgg cagggtttcg                                        20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 18
ttgcatatcg ccgtcatcgg                                        20

<210> SEQ ID NO 19
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 19
gctgacggaa tttatgcctc ttc                                    23

<210> SEQ ID NO 20
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 20
ttggttaatt ggttgtaaca ctggc                                  25

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 21
tgagggagcc acggttgatg                                        20

<210> SEQ ID NO 22
<211> LENGTH: 25
<212> TYPE: DNA

```
<213> ORGANISM: Artificial Sequence
<220> FEATURE:
<223> OTHER INFORMATION: oligonucleotide primer

<400> SEQUENCE: 22
cgatcgctgt aaaaggaca attac                                              25

<210> SEQ ID NO 23
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 23
cgttccgtgg caaagcaaaa                                                   20

<210> SEQ ID NO 24
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 24
tatctggcag agaacccgca gg                                                22

<210> SEQ ID NO 25
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 25
gctggctggt ttattgctga taa                                               23

<210> SEQ ID NO 26
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 26
cgataagtcg tgtcttaccg gg                                                22

<210> SEQ ID NO 27
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 27
tctgatgccg catagttaag cc                                                22

<210> SEQ ID NO 28
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 28
ttaaagggga cagattcagg gttt                                              24
```

<210> SEQ ID NO 29
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 29
gctgtccgcc tttacgagct t                                              21

<210> SEQ ID NO 30
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 30
ttgacacggt accggtcgac                                                20

<210> SEQ ID NO 31
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 31
gccattcgat ggtgtcaacg taa                                            23

<210> SEQ ID NO 32
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 32
ggaagggttg tttctgtaga                                                20

<210> SEQ ID NO 33
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 33
gaaggctttg agagaggagg                                                20

<210> SEQ ID NO 34
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 34
atggtcgaga acaaagtcac                                                20

<210> SEQ ID NO 35
<211> LENGTH: 20
<212> TYPE: DNA
<213> ORGANISM: Artificial Sequence
<220> FEATURE:
<223> OTHER INFORMATION: oligonucleotide primer

```
<400> SEQUENCE: 35
atctgatcct tcaactcagc                                              20

<210> SEQ ID NO 36
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 36
gtccacctac aacaaagctc                                              20
```